(12) United States Patent
Nandabalan et al.

(10) Patent No.: US 6,372,490 B1
(45) Date of Patent: Apr. 16, 2002

(54) NUCLEIC ACID ENCODING THE MDM INTERACTING PROTEIN

(75) Inventors: Krishnan Nandabalan, Guilford; Meijia Yang, East Lyme; Vincent Schulz, Madison, all of CT (US)

(73) Assignee: CuraGen Corporation, New Haven, CT (US)

(*) Notice: Subject to any disclaimer, the term of this patent is extended or adjusted under 35 U.S.C. 154(b) by 0 days.

(21) Appl. No.: 09/510,252

(22) Filed: Feb. 22, 2000

Related U.S. Application Data

(60) Provisional application No. 60/121,192, filed on Feb. 23, 1999, now abandoned, and provisional application No. 60/122,643, filed on Mar. 3, 1999, now abandoned.

(51) Int. Cl.$^7$ .......................... C12N 5/00; C12N 15/00; C12N 15/09; C12N 15/63; C12N 15/70; C12N 15/74; A01N 63/00; C07H 21/04

(52) U.S. Cl. .................. 435/325; 424/93.21; 435/69.3; 435/252.3; 435/320.1; 514/44; 536/23.5

(58) Field of Search ................ 536/23.5, 23.1; 435/320.1, 325, 252.3; 424/93.21; 514/44

(56) References Cited

FOREIGN PATENT DOCUMENTS

| WO | WO 93 20238 | 10/1993 |
|----|-------------|---------|
| WO | WO 96 02642 | 2/1996  |
| WO | WO 98 54206 | 12/1998 |

OTHER PUBLICATIONS

Gura (Science, 1997, 278:1041–1042).*
Jain (Sci. Am., 1994, 271:58–65).*
Curti (Crit. Rev. in Onocology/Hematology, 1993, 14:29–39).*
Hartwell et al (Science, 1997, 278:64–1068).*
Burgess et al. J of Cell Bio. 111:2129–2138, 1990.*
Lazar et al. Molecular and Cellular.*
Chien, et al., Proc Natl Acad Sci USA, 88 (21), 9578–9582 (1991).
Juven–Gershon et al., Mol Cell Biol, 18 (7), 3974–3982 (1998).
Martin et al., Nature, 375, 691–694 (1995).
Momand et al., Nucleic Acids Res, 26 (15), 3453–3459 (1998).
Oilner, et al., Nature, 358, 80–83 (1992).
Sohocki, et al., Genomics, 400 (2), 247–252 (1997).
Chen, J. et al., Mol. Cell Biol., 13, No. 7, 4107–4114 (1993).
Hillier, L. et al., EMBL, Accession No. N28611, Jan. 4 (1996).

* cited by examiner

Primary Examiner—Anthony Caputa
Assistant Examiner—Natalie Davis
(74) Attorney, Agent, or Firm—Mintz, Levin, Cohn, Ferris, Glovsky and Popeo, P.C.; Ivor R. Elrifi, Esq.

(57) ABSTRACT

Disclosed are complexes of the MDM2 protein and a novel MDM2-interacting protein (MDMIP). Also disclosed are nucleic acids encoding the MDMIP polypeptide, as well as derivatives, fragments, analogs and homologs of the MDMIP polypeptide and MDM2-MDMIP complexes.

4 Claims, 2 Drawing Sheets

Nucleic Acid Sequence and Encoded Amino Acid Sequence of a
Human MDMIP Polypeptide

```
  1
    GCACGAGCGTATNAAAAAATGTTTTCCATGTTTATGGAAAAGGCT
    A  R  A  Y  X  K  M  F  S  M  F  M  E  K  A
 46
    GGGAAGTGCTGGTGTAAAATGCCCAAGCTCATAATAGATACTCCT
    G  K  C  W  C  K  M  P  K  L  I  I  D  T  P
 91
    TTCTCCATTGTTGCCCCTGCTCTAACTGCTGTTCTTTCTTGCCAG
    F  S  I  V  A  P  A  L  T  A  V  L  S  C  Q
136
    CTTCGTTGTTCCCTCTGGCTTGTGGGGCACGGCTGTNCCATGT
    L  R  C  S  L  W  L  V  G  A  R  L  X  P  C
181
    GGCAAGGTGGAAGGCATGGACGTGTGGAGGAGGCGCTGGAGCTGA
    G  K  V  E  G  M  D  V  W  R  R  R  W  S   (SEQ ID NO:2)
226
    AGGAATGGACGAGCCCTGGGAGGAGGGCAGAAGGCTACGCAGGGC
271
    TGAGGATGAAGATGCAGCCCCTGGATNGTCCCCAGACTCTCAGGA
316
    CATTGCCCAGTCAAGGGTTCGAGCCACNAGGNCTTGGCTCATATG
361
    GCATGAAGGGGAACTTGCATAAGAAGCCCCCTCCCTGGTTGTGGT
406
    CCTGGCCCTCTGTTCTGGAAAACTGGNTCNTAGNCCCCCTGGTTT
451
    TTNGCAAAGCCTGAAGAAGGGAAANTCCCCATGGG  (SEQ ID NO:1)
```

Fig. 1

Nucleic Acid Sequence Encoding a MDMIP-Binding MDM2 Polypeptide
Fragment Derived from a Human MDM2 Polypeptide

```
 atgtgcaat accaacatgt ctgtacctac tgatggtgct gtaaccacct cacagattcc agcttcggaa
caagagaccc tggttagacc aaagccattg cttttgaagt tattaaagtc tgttggtgca caaaaagaca
cttatactat gaaagaggtt cttttttatc ttggccagta tattatgact aaacgattat atgatgagaa
gcaacaacat attgtatatt gttcaaatga tcttctagga gatttgtttg gcgtgccaag cttctctgtg
aaagagcaca ggaaaatata taccatgatc tacaggaact tggtagtagt caatcagcag gaatcatcgg
actcaggtac atctgtgagt gagaacaggt gtcaccttga aggtgggagt gatcaaaagg accttgtaca
agagcttcag gaagagaaac cttcatcttc acatttggtt tctagaccat ctacctcatc tagaaggaga
gcaattagtg agacagaaga aaattcagat gaattatctg gtgaacgaca agaaaacgc cacaaatctg
atagtatttc cctttccttt gatgaaagcc tggctctgtg tgtaataagg gagatatgtt gtgaaagaag
cagtagcagt gaatctacag gga   (SEQ ID NO:3)
```

Fig. 2A

Amino Acid Sequence of MDMIP-Binding MDM2 Polypeptide Fragment
Derived from a Human MDM2 Polypeptide MCNTNMSVPTDGAVTTSQIPASEQETLVRPKPLLLKLLKSVGAQKDTYTM
KEVLFYLQYIMTKRLYDEKQQHIVYCSNDLLGDLFGVPSFSVKEHRKIYT
MIYRNLVVVNQQESSDSGTSVSENRCHLEGGSDQKDLVQELQEEKPSSSH
LVSRPSTSSRRRAISETEENSDELSGERQRKRHKSDSISLSFDESLALCV
IREICCERSSSSESTG (SEQ ID NO:4)

Fig. 2B

NUCLEIC ACID ENCODING THE MDM INTERACTING PROTEIN

RELATED APPLICATIONS

This application claims priority from U.S. Ser. No. 60/121,192, abandoned filed Feb. 23, 1999 and U.S. Ser. No. 60/122,643, abandoned filed Mar. 3, 1999. The contents of these applications are incorporated herein by reference in their entirety.

STATEMENT OF GOVERNMENT SUPPORT

This invention was made with United States Government support under award number 70NANB5H1066 awarded by the National Institute of Standards and Technology. The United States Government has certain rights in the invention.

FIELD OF THE INVENTION

The invention relates generally to polypeptides and nucleic acids and more particularly to polypeptides that interact with the MDM2 polypeptide, and nucleic acids encoding these MDM2-interacting polypeptides.

BACKGROUND OF THE INVENTION

The gene MDM2 has been implicated in a variety of cellular processes. In addition, altered expression of MDM2 has been associated with several disease states, including cancer. For example, the MDM2 gene has been shown to be abnormally up-regulated in human tumors and tumor cell lines. In addition, amplification of MDM2 genes has been reported in a variety of cancers, e.g., human sarcoma, glioma, squamous cell carcinoma, breast cancer, astrocytoma, leukemia and lymphoma. These results indicate that the MDM2 protein plays a role in human carcinogenesis.

MDM2 has been reported to interact with, i.e., bind to other proteins. Some of these proteins have themselves been associated with tumorigenesis. For example, MDM2 has been reported to form a complex with the p53 tumor suppressor and to block the growth suppressive functions of p53. In addition, overexpression of MDM2 has been shown to block the transactivation, cell cycle arrest (S/G2 phase) and apoptotic functions of p53.

MDM2 has also been shown to interact with the retinoblastoma tumor suppressor protein pRb, and the E2F-1 and DP1 transcription factors. Through MDM2's activation of E2F and DP1, MDM2 is thought to stimulate a G1 to S transition in the cell cycle. In addition, MDM2 has also been reported to interact with Numb, a protein involved in the determination of cell fate.

SUMMARY OF THE INVENTION

The invention is based in part on the discovery of a novel polypeptide, named MDM Interacting Protein, or "MDMIP", based on its ability to bind to the MDM2 polypeptide.

In one aspect, the invention includes a purified complex that includes a polypeptide which includes an MDMIP binding domain (or region) of an MDM2 polypeptide and a polypeptide which includes an MDM2 binding domain (or region) of an MDMIP polypeptide. The complex can thus include, e.g, an MDM2 polypeptide and an MDMIP polypeptide. In various embodiments, the MDM2 polypeptide, the MDMIP polypeptide, or both polypeptides within the complex, are human polypeptides.

In some embodiments, the MDM2 binding domain of the MDM2 polypeptide includes an amino acid sequence that is at least 70%, 75%, 80%, 85%, 90%, 95%, 98%, or 99% or more identical to the amino acid sequence of a region of polypeptide that includes the amino acid sequence of SEQ ID NO:2.

In some embodiments, the MDMIP binding domain of the MDM2 polypeptide includes an amino acid sequence that is at least 70%, 75%, 80%, 85%, 90%, 95%, 98%, or 99% or more identical to the amino acid sequence of a region of polypeptide that includes the amino acid sequence encoded by the nucleic acid sequence having GenBank accession number M92424. In some embodiments, the MDMIP binding domain includes the amino acid sequence of SEQ ID NO:4, e.g., it can include the amino acid sequence of the MDM2 polypeptide encoded by the nucleic acid sequence of M9424 (SEQ ID NO:6). Thus, in some embodiments, the MDMIP binding domain of the MDM2 polypeptide is present in a polypeptide which includes the amino acid sequence of an MDM2 polypeptide, e.g., a polypeptide including at least that portion of the amino acid sequence of SEQ ID NO:4 that is sufficient to bind to an MDMIP polypeptide.

If desired, one or more of the polypeptides in the MDM2-MDMIP complex, e.g., the MDM2-binding domain of the MDMIP polypeptide, the MDMIP-binding domain of the MDM2 polypeptide, or both is labeled.

In other embodiments, the complex includes a fragment of an MDMIP polypeptide that includes an MDM2-binding domain, a fragment of an MDM2 polypeptide that includes an MDMIP-binding domain, or both fragments.

Another aspect of the invention includes a chimeric polypeptide that includes a region of an MDMIP polypeptide covalently linked, e.g., via a peptide bond, to a region of an MDM2 polypeptide. Preferably, the chimeric peptide includes 6, 8, 10, 12, 14, or 16 or more amino acids of an MDM2 polypeptide covalently linked to 6, 8, 10, 12, 14, 16 or more amino acids of an MDMIP polypeptide.

In some embodiments, the amino acids of the MDMIP-derived polypeptide in the chimeric polypeptide include an MDM2 binding domain. For example, the MDMIP-derived polypeptide can include a polypeptide which binds to MDM2 and, optionally, includes at least a portion of an amino acid sequence at least 80%, 85%, 90%, 95%, 98%, or 99% or more identical to the amino acid sequence of SEQ ID NO:2.

Similarly, in some embodiments, the amino acids of the MDM2-derived polypeptide in the chimeric polypeptide include an MDMIP-binding domain. Thus, the MDM2 polypeptide can include a polypeptide which binds to MDMIP and, optionally, includes at least a portion of an amino acid sequence at least 80%, 85%, 90%, 95%, 98%, or 99% or more identical to the amino acid sequence of SEQ ID NO:4, i.e., a polypeptide having the amino acid sequence encoded by nucleic acids 312–963 of the nucleic acid sequence corresponding to GenBank accession number M92424.

In a further aspect, the invention includes an isolated MDMIP nucleic acid. In some embodiments, the MDMIP nucleic acid encodes an MDMIP polypeptide, e.g., the nucleic acid may include a nucleic acid that encodes a polypeptide at least 70%, 75%, 80%, 85%, 90%, 95%, 98% or even 99% identical to a polypeptide which includes the amino acid sequence of SEQ ID NO:2.

The MDMIP nucleic acid may alternatively, or in addition, include a sequence that is at least 70%, 75%, 80%, 85%, 90%, 95%, 98% or even 99% identical to a nucleic acid which includes nucleic acids 1–222 of FIG. 1 (SEQ ID NO:1).

Also provided by the invention is a vector including an MDMIP nucleic acid, as well as a cell that includes an MDMIP nucleic acid. The MDMIP nucleic acid in the cell may be present in a vector, i.e., the invention includes a cell that contains a vector in which an MDMIP nucleic acid is present.

Another aspect of the invention includes a purified MDMIP polypeptide with an amino acid sequence at least 70%, 75%, 80%, 85%, 90%, 95%, 98%, or even 99% or more identical to the amino acid sequence of SEQ ID NO:2. In some embodiments, the MDMIP polypeptide binds to an MDM2 polypeptide.

In a further aspect, the invention includes an isolated MDM2-derived nucleic acid fragment. The MDM2-derived nucleic acid is less than the full length of a full-length MDM2 nucleic acid, i.e., the nucleic acid includes less than the full length reading frame of a nucleic acid encoding a full length MDM2 polypeptide. In some embodiments, the MDM2-derived nucleic acid encodes an MDM2polypeptide fragment that is less than 491 amino acids, e.g, it is less than 450, 400, 350, 300, 250, 200, 150, 100, or 50 amino acids, and, optionally, binds an MDMIP polypeptide, e.g., a polypeptide having the amino acid sequence of SEQ ID NO:2. Alternatively, or in addition, the MDM2-derived nucleic includes a nucleic acid that encodes a polypeptide at least 70%, 75%, 80%, 85%, 90%, 95%, 98% or even 99% identical to a polypeptide which includes the amino acid sequence of SEQ ID NO:4, and which is less than 491 amino acids in length and is greater than 4 amino acids in length. Preferably, the MDMIP-binding polypeptide is greater than 5, 6, 7, 8, 9, or 10 amino acids in length and is less than 25, 50, 75, 100, 150, 200, 250, 300, 350, 400 or 450 amino acids in length.

The MDM2-derived nucleic acid may alternatively, or in addition, include a sequence that is at least 70%, 75%, 80%, 85%, 90%, 95%, 98% or even 99% identical to a nucleic acid which includes the nucleic acid sequence of SEQ ID NO:3.

Also provided by the invention is a vector including the MDM2-derived nucleic acid, as well as a cell that includes an MDM2-derived nucleic acid. The MDM2-derived nucleic acid in the cell may be present in a vector, i.e., the invention includes a cell that contains a vector in which an MDM2-derived nucleic acid is present.

Another aspect of the invention includes a purified MDM2 polypeptide with an amino acid sequence at least 70%, 75%, 80%, 85%, 90%, 95%, 98%, or even 99% or more identical to a polypeptide that includes the amino acid sequence of SEQ ID NO:4.

Also provided by the invention are antibodies (e.g., polyclonal or monoclonal antibodies) that bind to the MDMIP-MDM2 complexes described herein. For example, the invention includes an antibody which specifically binds to a complex that includes a polypeptide that has an MDMIP binding domain of an MDM2 polypeptide and a polypeptide that includes an MDM2 binding domain of an MDMIP polypeptide. In some embodiments, the antibody binds with higher affinity to a complex that includes an MDMIP binding domain of an MDM2 polypeptide and an MDM2 binding domain of an MDMIP polypeptide as compared to the binding of the antibody to an isolated MDM2 polypeptide or an isolated MDMIP polypeptide.

The invention also includes antibodies (e.g, polyclonal or monoclonal antibodies) that bind to an MDMIP polypeptide, or to an MDMIP-binding fragment of an MDM2 polypeptide. These antibodies, in various embodiments, may optionally bind to the herein described MDM2-MDMIP complexes as well.

In a further aspect, the invention features a pharmaceutical composition that includes one or more of an MDMIP polypeptide, and MDMIP nucleic acid, a chimeric polypeptide containing sequences derived from an MDM2 polypeptide and sequences derived from an MDMIP polypeptide, and a complex of an MDM2-binding domain of an MDMIP polypeptide and an MDM2-binding domain of an MDMIP polypeptide. The pharmaceutical composition may alternatively, or additionally, contain an antibody to any of these polypeptides, nucleic acids or complexes.

Also included in the invention is a kit containing reagents that detect one or more of an MDMIP polypeptide, and MDMIP nucleic acid, a chimeric polypeptide containing sequences derived from an MDM2 polypeptide and sequences derived from an MDMIP polypeptide, and a complex of an MDM2-binding domain of an MDMIP polypeptide and an MDM2-binding domain of an MDMIP polypeptide. In some embodiments, the reagents can include one or more of an antibody to an MDM2 polypeptide, an antibody to and MDMIP polypeptide, and/or an antibody to a complex of an MDM2-binding domain of an MDMIP polypeptide and an MDM2-binding domain of an MDMIP polypeptide. The reagent may in addition include the MDMIP polypeptide for detecting the presence of MDM2 in a sample, an MDM2 protein for detecting the presence of MDMIP in a sample.

The invention also includes methods of identifying a MDM2-MDMIP complex, or various components of an MDM2-MDMIP complex, in a biological sample. For example, the invention includes a method of identifying a MDM2 sample in a biological sample by contacting the biological sample with an MDMIP polypeptide under conditions allowing for the formation of MDM2-MDMIP complexes. Levels of the MDM2-MDMIP complex, if present, are then determined, thus allowing for determination of levels of MDM2 polypeptide in the cell.

In some embodiments, MDM2 polypeptides are detected using a labeled MDMIP polypeptide. Detection of labeled MDMIP-MDM2 complexes indicates the presence of a MDM2 polypeptide in the sample.

The invention also features a method of purifying an MDM2 polypeptide from a biological sample by contacting the biological sample with a polypeptide that includes an MDM2-binding region of an MDMIP polypeptide.

Also included in the invention is a method of identifying an agent which modulates MDM2 or MDMIP activity. The method includes contacting a test agent with an MDM-MDMIP complex and measuring binding of the agent to the complex. Binding of the agent to the complex indicates the agent modulates MDM2 or MDMIP polypeptide activity.

In another aspect, the invention includes a method of identifying an agent which modulates MDMIP activity. In this method an MDMIP polypeptide is mixed with a test agent and binding of the agent to the complex is measured. Binding of the agent to the complex indicates the agent modulates MDMIP polypeptide activity.

The invention also includes a method of determining whether a test subject has a disorder associated with aberrant expression of MDM2 protein. The method includes providing a biological sample from the subject, measuring the level of the complex in the subject; and comparing the level of complex in the sample to the level of the complex in a reference sample whose MDM2 expression state is known. Comparing the relative levels of the MDM2 protein in the two samples makes it possible to determine whether the subject has a disorder associated with aberrant expression of an MDM2 protein.

Yet another aspect of the invention is a method of treating or preventing a disease or disorder involving aberrant levels of a complex of a MDM2 protein and a MDMIP. The method includes administering to a subject in which such treatment or prevention is desired a therapeutically-effective amount of a molecule or molecules which are capable of modulating the function of the complex.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 1 is a schematic representation of the nucleotide sequence (SEQ ID NO:7) of a human MDMIP polypeptide, along with an encoded amino acid sequence (SEQ ID NO:2). Nucleic acids 1–222 (SEQ ID NO:1) encode the shown amino acid sequence.

FIGS. 2A and B are schematic representations of the nucleotide sequence (SEQ ID NO:3) (FIG. 2A) and the amino acid sequence (SEQ ID NO:4) of an MDMIP binding fragment of a human MDM2 cDNA (FIG. 2B).

DETAILED DESCRIPTION OF THE INVENTION

The present invention is based in part on the identification of a novel polypeptide, named "MDMIP", which was discovered based on its ability to bind to a fragment of a human MDM2 polypeptide.

The MDMIP polypeptide was identified in a yeast two hybrid system designed to identify proteins ("target") based on their ability to bind specifically to, i.e., interact with, a known protein ("bait protein"). The bait protein used to identify interacting fragments was a cDNA fragment containing nucleotides 312 to 963 (SEQ ID NO:3) of the human MDM2 cDNA having GenBank Accession Number M492424. The nucleotide sequence encoding the MDM2 bait polypeptide fragment is shown in FIG. 2 as SEQ ID NO:3. The amino acid sequence of the encoded bait polypeptide fragment is shown in FIG. 2 as SEQ ID NO:4 The full length sequence of the human MDM2 nucleic acid is from GenBank Accession Number M92424 (SEQ ID NO:5). The amino acid sequence of the MDM2 polypeptide encoded by this nucleic acid is SEQ ID NO:6.

Five polypeptides were determined to the MDM2-derived bait polypeptide in the assay. Four of those corresponded to previously described proteins. These polypeptides include human p53 cellular tumor antigen (GenBank Acc. No. X54156), retinoblastoma protein (pRB; GenBank Acc. No. M28419), E2F-1 (a pRB-binding protein with properties of transcription factor E2F) nucleic acid sequence (GenBank Acc. No. M96577), and ubiquitin (GenBank Acc. No. U49869).

One interacting protein, however had not been previously described. It was named MDMIP, for MDM Interacting Protein. The nucleic acid sequence of a human cDNA encoding an MDMIP polypeptide is shown in FIG. 1 as SEQ ID NO:1. The amino acid sequence of the polypeptide encoded by this nucleic acid sequence is shown as SEQ ID NO:2. Because no initiation codon is present in the reading frame, it is possible that the sequence shown in FIG. 1 is a partial sequence of a human MDMIP cDNA. The disclosed sequence may correspond to the amino acid sequence at the carboxy terminal region of a human MDMIP polypeptide.

Included within the invention are MDMIP nucleic acids and their encoded polypeptides. Also disclosed are MDMIP-interacting MDM2-derived polypeptides, as well as complexes that include MDM2-binding MDMIP polypeptides and MDMIP-binding MDM2 polypeptides and chimeric polypeptides containing MDM2 binding MDMIP polypeptides and MDMIP binding MDM2 polypeptides. Also disclosed are antibodies to these polypeptides and complexes, as well as pharmaceutical compositions and methods utilizing these nucleic acids, polypeptides, and complexes.

MDMIP Nucleic Acids

Included in the invention is an MDMIP nucleic acid. By "MDMIP nucleic acid" is meant a nucleic acid which is at least 70% identical to a nucleic acid including the nucleic acid sequence of SEQ ID NO:1. Also included in the term "MDMIP nucleic acid" is a nucleic acid fragment that includes a portion of a sequence at least 70% identical to a nucleic acid including the nucleic acid sequence of SEQ ID NO:1, provided that the fragment contains enough sequence to specifically hybridize to a sequence at least 70% identical to a nucleic acid including the nucleic acid sequence of SEQ ID NO:1. Additional examples of MDMIP nucleic acids include nucleic acids 1–442 of FIG. 1.

In some embodiments, the MDMIP nucleic acid encodes an MDMIP polypeptide. By "MDMIP polypeptide" is meant a polypeptide at least 70% identical to the amino acid sequence of a polypeptide that includes the amino acid sequence of SEQ ID NO:2.

In some embodiments, the MDMIP nucleic acid encodes an MDMIP polypeptide that includes an MDM2 binding domain. By "MDM2-binding domain" is meant a region of amino acids sufficient to allow the polypeptide in which the region of amino acids is present to bind specifically to an MDM2 polypeptide. The encoded MDM2-binding polypeptide can be derived from a full-length MDMIP polypeptide, or from a derivative, fragment, analog, homolog or paralog of an MDMIP polypeptide. Preferably, the derivative, fragment, analog, homolog or paralog the has one or more of the following attributes: (i) is functionally active (i.e., capable of exhibiting one or more functional activities associated with full-length, wild-type MDMIP; (ii) possesses the ability to bind the MDM2 protein; (iii) is immunogenic or (iv) is antigenic.

In some embodiments, the fragment of an MDMIP polypeptide includes at least 10, 20, 30, 40, or 50 amino acid residues (preferably not larger that 35, 100 or 200 amino acid residues) of the MDMIP polypeptide. Derivatives or analogs of the encoded MDMIP polypeptide include, e.g., molecules which include regions which are substantially homologous to the MDM2 protein or MDMIP in various embodiments, of at least 50%, 60%, 70%, 80%, 90% or 95% amino acid identity when: (i) compared to an amino acid sequence of identical size; (ii) compared to an aligned sequence in which the alignment is done by a computer homology program known within the art or (iii) the encoding nucleic acid is capable of hybridizing to a sequence encoding the MDM2 protein or MDMIP under stringent, moderately stringent, or non-stringent conditions, as is discussed below.

Thus, in some embodiments, the encoded MDM2-binding domain is derived from an MDMIP polypeptide that includes a sequence that is at least 90% identical to a polypeptide which includes the amino acid sequence of SEQ ID NO:2. In some embodiments, the domain is derived from an MDMIP polypeptide which is at least 95, 98 or even 99% identical to a polypeptide including the amino acid sequence of SEQ ID NO:2.

In some embodiments, the encoded MDMIP polypeptide is a polypeptide which includes the amino acid sequence of SEQ ID NO:2. For example, the MDMIP polypeptide may correspond to some or all of the amino acid sequences encoded by the longest open reading frame present in a nucleic acid that includes SEQ ID NO:1. Alternatively, the MDMIP polypeptide can include a region of the amino acid sequence of SEQ ID NO:2 that is able to bind specifically to an MDM2 polypeptide.

Procedures for identifying regions within SEQ ID NO:2 that bind to MDM2 can be readily identified by one of ordinary skill in the art. In addition, the sequence information disclosed herein for MDMIP, e.g., the nucleic acid and amino acid sequences disclosed in FIG. 1, may be combined with any method available within the art to obtain longer clones encompassing additional MDMIP coding sequences. Such sequences, for example, may encode an initiator codon for an MDMIP polypeptide.

For example, the polymerase chain reaction (PCR) may be utilized to amplify the sequence within a cDNA library. Similarly, oligonucleotide primers may also be used to amplify by PCR sequences from a nucleic acid sample (RNA or DNA), preferably a cDNA library, from an appropriate source (e.g., the sample from which the initial cDNA library for the modified yeast two hybrid assay fusion population was derived).

PCR may be performed by use of, for example, a thermal cycler and Taq polymerase. The DNA being amplified is preferably cDNA derived from any eukaryotic species. Several different degenerate primers may be synthesized for use in the PCR reactions. It is also possible to vary the stringency of the hybridization conditions used in priming the PCR reactions, to amplify nucleic acid homologs by allowing for greater or lesser degrees of nucleotide sequence similarity between the known nucleotide sequence and the nucleic acid homolog being isolated. For cross species hybridization, low stringency conditions are preferred; whereas for same species hybridization, moderately stringent conditions are preferred.

Any eukaryotic cell may potentially serve as the nucleic acid source for the molecular cloning of the MDMIP sequences. The DNA may be obtained by standard procedures known in the art from cloned DNA (e.g., a DNA "library"), by chemical synthesis, by cDNA cloning, or by the cloning of genomic DNA, or fragments thereof, purified from the desired cell. See e.g., Sambrook, et al., 1989. *Molecular Cloning: A Laboratory Manual*, 2nd ed., (Cold Spring Harbor Laboratory Press, Cold Spring Harbor, N.Y.); and Glover, 1985. *DNA Cloning: A Practical Approach* (MRL Press, Ltd., Oxford, U.K. Vol. I, II). Clones derived from genomic DNA may contain regulatory and intronic DNA regions in addition to exonic (coding) regions; whereas clones derived from cDNA will contain only exonic sequences.

MDMIP nucleic acids are preferably derived from a cDNA source. Identification of the specific cDNA containing the desired sequence may be accomplished in a number of ways. In one method, a portion of the MDMIP sequence (e.g., a PCR amplification product obtained as described above), or an oligonucleotide possessing a sequence of a portion of the known nucleotide sequence, or its specific RNA, or a fragment thereof, may be purified, amplified, and labeled, and the generated nucleic acid fragments may be screened by nucleic acid hybridization utilizing a labeled probe. See e.g., Benton & Davis, 1977. *Science* 196:180. In a second method, the appropriate fragment is identified by restriction enzyme digestion(s) and comparison of fragment sizes with those expected from comparison to a known restriction map (if such is available) or by DNA sequence analysis and comparison to the known nucleotide sequence of MDMIP. In a third method, the gene of interest may be detected utilizing assays based on the physical, chemical or immunological properties of its expressed product. For example, cDNA clones, or DNA clones which hybrid-select the proper mRNAs, may be selected as a function of heir production of a protein which, for example, has similar or identical electrophoretic migration, isoelectric focusing behavior, proteolytic digestion maps, antigenic properties or ability to bind the MDM2 protein. In a fourth method, should an anti-MDMIP antibody be available, the protein of interest may be identified by the binding of a labeled antibody to the putatively MDMIP clone in an enzyme-linked immunosorbent assay (ELISA).

The MDMIP nucleic acid can be an isolated nucleic acid. An "isolated" nucleic acid molecule is one that is separated from other nucleic acid molecules which are present in the natural source of the nucleic acid. Examples of isolated nucleic acid molecules include, e.g., recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated MDMIP nucleic acid molecule can contain less than about 50 kb, 25 kb, 5 kb, 4 kb, 3 kb, 2 kb, 1 kb, 0.5 kb or 0.1 kb of nucleotide sequences which natural flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, e.g., a nucleic acid molecule including the nucleotide sequence of SEQ ID NO:1, and/or encoding the polypeptide including the amino acid sequence of SEQ ID NO:1, or a complement of any of these nucleotide sequences, can be isolated using standard molecular biology techniques and the sequence information provided herein. Using all or a portion of the nucleic acid sequences of SEQ ID NO:1 as a hybridization probe, MDMIP nucleic acid sequences can be isolated using standard hybridization and cloning techniques (e.g., as described in Sambrook et al., eds., MOLECULAR CLONING: A LABORATORY MANUAL 2nd Ed., Cold Spring Harbor Laboratory Press, Cold Spring Harbor, N.Y., 1989; and Ausubel, et al., eds., CURRENT PROTOCOLS IN MOLECULAR BIOLOGY, John Wiley & Sons, New York, N.Y., 1993.).

In some embodiments, the MDMIP nucleic acid is identical in sequence to a nucleic acid that includes SEQ ID NO:1. In other embodiments, the MDMIP nucleic acid differs from the nucleic acid sequence of a nucleic acid that includes SEQ ID NO:1. For example, the MDMIP nucleic acid may include a sequence at least 90%, 95%, 98%, or even 99% or more identical to the nucleic acid sequence of SEQ ID NO:1. These sequences are referred to herein as variant MDMIP nucleic acid sequences. An alternative way to describe variant MDMIP nucleic acid sequences is to describe nucleic acids that hybridize to a sequence including SEQ ID NO:1, or to an MDM2-binding fragment of SEQ ID NO:1.

To determine the percent relatedness of two nucleic acid sequences, or of two amino acid sequences (e.g., as would be done to compare variant MDMIP polypeptides as discussed in more detail below, or nucleic acids encoding such variant polypeptides), the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See Needleman and Wunsch 1970 J Mol Biol 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of a DNA sequence including the nucleic acid shown in SEQ ID NO:1 or a polypeptide including the amino acid sequence shown in SEQ ID NO:2.

The term "sequence identity" refers to the degree to which two polynucleotide or polypeptide sequences are identical on a residue-by-residue basis over a particular region of comparison. Sequence identity can be measured using sequence analysis software (Sequence Analysis Software Package of the Genetics Computer Group, University of Wisconsin Biotechnology Center, 1710 University Avenue, Madison, Wis. 53705), with the default parameters therein.

The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

DNA sequence polymorphisms that lead to changes in the amino acid sequences of an MDMIP polypeptide may exist within a population (e.g., the human population). Such genetic polymorphism in the MDMIP gene may exist among individuals within a population due to natural allelic variation. As used herein, the terms "gene" and "recombinant gene" refer to nucleic acid molecules comprising an open reading frame encoding a MDMIP polypeptide, preferably a mammalian MDMIP polypeptide. Such natural allelic variations can typically result in 1–5% variance in the nucleotide sequence of the polypeptide gene. Any and all such nucleotide variations and resulting amino acid polymorphisms in MDMIP that are the result of natural allelic variation and that do not alter the functional activity of MDMIP are intended to be within the scope of the invention.

Moreover, nucleic acid molecules encoding MDMIP proteins from other species, and thus that have a nucleotide sequence that differs from the human sequence of SEQ ID NO:1, are intended to be within the scope of the invention. Nucleic acid molecules corresponding to natural allelic variants and homologues of the MDMIP cDNAs of the invention can be isolated based on their homology to the human MDMIP nucleic acids disclosed herein using the human cDNAs, or a portion thereof, as a hybridization probe according to standard hybridization techniques under stringent hybridization conditions. For example, a soluble human MDMIP cDNA can be isolated based on its homology to human membrane-bound MDMIP. Likewise, a membrane-bound human MDMIP cDNA can be isolated based on its homology to soluble human MDMIP.

Accordingly, in another embodiment, an isolated nucleic acid molecule of the invention is at least 6 nucleotides in length and hybridizes under stringent conditions to the nucleic acid molecule comprising the nucleotide sequence of SEQ ID NO:1. In another embodiment, the nucleic acid is at least 10, 25, 50, 100, 250 or 500 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding MDMIP proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in CURRENT PROTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. An isolated nucleic acid molecule of the invention that hybridizes under stringent conditions to the sequence of SEQ ID NO:1 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NO:1, or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well known in the art. See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY.

In a third embodiment, a nucleic acid that is hybridizable to the nucleic acid molecule comprising the nucleotide sequence of SEQ ID NO:1, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981, Proc Natl Acad Sci USA 78: 6789–6792.

In addition to naturally-occurring allelic variants of the MDMIP sequence that may exist in the population, an MDMIP nucleic acid also includes nucleic acids including changes introduced by alteration of the nucleotide sequence of SEQ ID NO:1. In some embodiments, these changes lead to changes in the amino acid sequence of the encoded MDMIP protein, without altering the functional ability of the MDMIP protein. For example, nucleotide substitutions leading to amino acid substitutions at "non-essential" amino acid residues can be made in the sequence of SEQ ID NO:1. A "non-essential" amino acid residue is a residue that can be altered from the wild-type sequence of MDMIP without altering the biological activity, whereas an "essential" amino acid residue is required for binding to MDM2 or for a biological activity mediated by an MDMIP polypeptide. For example, amino acid residues that are conserved among the MDMIP proteins of the present invention, are predicted to be particularly unamenable to alteration.

In addition, amino acid residues that are conserved among family members of the MDMIP proteins of the present invention, are also predicted to be particularly unamenable to alteration. Other amino acid residues, however, (e.g., those that are not conserved or only semi-conserved among members of the MDMIP proteins) may not be essential for activity and thus are likely to be amenable to alteration.

Another aspect of the invention pertains to nucleic acid molecules encoding MDMIP proteins that contain changes in amino acid residues that are not essential for activity. Such MDMIP proteins differ in amino acid sequence from SEQ ID NO:2, yet retain biological activity (e.g., MDM2-binding activity). In one embodiment, the isolated nucleic acid molecule comprises a nucleotide sequence encoding a protein, wherein the protein comprises an amino acid sequence at least about 45% homologous to the amino acid sequence of SEQ ID NO:2. Preferably, the protein encoded by the nucleic acid molecule is at least about 60% homologous to SEQ ID NO:2, more preferably at least about 70%, 80%, 90%, 95%, 98%, and most preferably at least about 99% homologous to SEQ ID NO:2.

An isolated nucleic acid molecule encoding a MDMIP protein homologous to the protein of SEQ ID NO:2 can be created by introducing one or more nucleotide substitutions, additions or deletions into the nucleotide sequence of SEQ ID NO:1, such that one or more amino acid substitutions, additions or deletions are introduced into the encoded protein.

Mutations can be introduced into SEQ ID NO:1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in MDMIP is replaced with another amino acid residue from the same side chain family. Alternatively, in another embodiment, mutations can be introduced randomly along all or part of a MDMIP coding sequence, such as by saturation mutagenesis, and the resultant mutants can be screened for MDMIP biological activity to identify mutants that retain activity. Following mutagenesis of SEQ ID NO:1 , the encoded protein can be expressed by any recombinant technology known in the art and the activity of the protein can be determined.

In one embodiment, a mutant MDMIP polypeptide can be assayed for (1) the ability to form protein:protein interactions with other MDMIP proteins, or biologically active portions thereof, (2) the ability to form complexes with form complexes with MDM2 polypeptides, (3) the ability to form complexes with a mutant MDMIP protein and a MDMIP ligand (including MDMIP binding domains of MDM2 polypeptides, or other MDMIP ligands); (4) the ability of a mutant MDMIP protein to bind to an intracellular target protein or biologically active portion thereof, (e.g., avidin proteins); (5) the ability to bind ATP; or (6) the ability to specifically a MDMIP protein antibody.

If desired, MDMIP nucleic acids can be derived from a cDNA source. Identification of the specific cDNA containing the desired sequence may be accomplished in a number of ways. In one method, a portion of the MDMIP sequence (e.g., a PCR amplification product), or an oligonucleotide possessing a sequence of a portion of the known nucleotide sequence, or its specific RNA, or a fragment thereof, may be purified, amplified, and labeled, and the generated nucleic acid fragments may be screened by nucleic acid hybridization utilizing a labeled probe. See e.g., Benton & Davis, Science 196:180, 1977. In a second method, the appropriate fragment is identified by restriction enzyme digestion(s) and comparison of fragment sizes with those expected from comparison to a known restriction map (if such is available) or by DNA sequence analysis and comparison to the known nucleotide sequence of MDMIP. In a third method, the gene of interest may be detected utilizing assays based on the physical, chemical or immunological properties of its expressed product. For example, cDNA clones, or DNA clones which hybrid-select the proper mRNAs, may be selected as a function of their production of a protein which, for example, has similar or identical electrophoretic migration, isolectric focusing behavior, proteolytic digestion maps, antigenic properties or ability to bind the MDM2 protein. In a fourth method, should an anti-MDMIP antibody be available, the protein of interest may be identified by the binding of a labeled antibody to the putatively MDMIP clone in an enzyme-linked immunosorbent assay (ELISA).

Also included in the invention are vectors that include MDMIP nucleic acids, as well as cells containing MDMIP nucleic acids or vectors containing MDMIP nucleic acids. In general, any suitable vector known in the art can be used. For recombinant expression of an MDMIP polypeptide, a nucleic acid containing all or a portion of the nucleotide sequence encoding the polypeptide may be inserted into an appropriate expression vector (i.e., a vector which contains the necessary elements for the transcription and translation of the inserted protein coding sequence). The regulatory elements can be heterologous (i.e., not the native gene promoter), or can be supplied by the native promoter for the MDMIP polypeptide, or any MDMIP genes and/or their flanking regions.

Exemplary host-vector systems that may be used to propagate MDMIP nucleic acids, or to express MDMIP polypeptides include, e.g.: (i) mammalian cell systems which are infected with vaccinia virus, adenovirus; (ii) insect cell systems infected with baculovirus; (iii) yeast containing yeast vectors or (iv) bacteria transformed with bacteriophage, DNA, plasmid DNA, or cosmid DNA. Depending upon the host-vector system utilized, any one of a number of suitable transcription and translation elements may be used.

The expression of the specific proteins may be controlled by any promoter/enhancer known in the art including, e.g: (i) the SV40 early promoter (see e.g., Bernoist & Chambon, Nature 290:304–310, 1981); (ii) the promoter contained within the 3'-terminus long terminal repeat of Rous Sarcoma Virus (see e.g., Yamamoto, et al., Cell 22:787–797, 1980); (iii) the Herpesvirus thymidine kinase promoter (see e.g, Wagner, et al., Proc. Natl. Acad. Sci. USA 30 78:1441–1445, 1981); (iv) the regulatory sequences of the metallothionein gene (see e.g., Brinster, et al., Nature 296:39–42, 1982); (v) prokaryotic expression vectors such as the β-lactamase promoter (see e.g., Villa-Kamaroff, et al., Proc. Natl. Acad. Sci. USA 75:3727–3731, 1978); (vi) the tac promoter (see e.g., DeBoer, et al., Proc. Natl. Acad. Sci. USA 80:21–25, 1983).

Plant promoter/enhancer sequences within plant expression vectors may also be utilized including, e.g.,: (i) the nopaline synthetase promoter (see e.g., Herrar-Estrella, et al., Nature 303:209–213, 1984); (ii) the cauliflower mosaic virus 35S RNA promoter (see e.g., Garder, et al., Nuc. Acids Res. 9:2871, 1981) and (iii) the promoter of the photosynthetic enzyme ribulose bisphophate carboxylase (see e.g., Herrera-Estrella, et al., Nature 310:115–120, 1984).

Promoter/enhancer elements from yeast and other fungi (e.g., the Gal4 promoter, the alcohol dehydrogenase promoter, the phosphoglycerol kinase promoter, the alkaline phosphatase promoter), as well as the following animal transcriptional control regions, which possess tissue specificity and have been used in transgenic animals, may be utilized in the production of proteins of the present invention.

Other animal transcriptional control sequences derived from animals include, e.g.,: (i) the insulin gene control region active within pancreatic β-cells (see e.g., Hanahan, et al., Nature 315:115–122, 1985); (ii) the immunoglobulin gene control region active within lymphoid cells (see e.g., Grosschedl, et al., Cell 38:647–658, 1984); (iii) the albumin gene control region active within liver (see e.g., Pinckert, et al., Genes and Devel. 1:268–276, 1987); (iv) the myclin basic protein gene control region active within brain oligodendrocyte cells (see e.g., Readhead, et al., Cell 48:703–712, 1987); and (v) the gonadotrophin-releasing hormone gene control region active within the hypothalamus (see e.g., Mason, et al., Science 234:1372–1378, 1986).

In one embodiment, the vector includes a promoter operably-linked to nucleic acid sequences which encode an MDMIP polypeptide, or a fragment, derivative or homolog, thereof, one or more origins of replication, and optionally, one or more selectable markers (e.g., an antibiotic resistance gene). If desired, a vector is utilized which includes a promoter operably-linked to nucleic acid sequences encoding both the MDM2 protein and MDMIP, one or more origins of replication, and, optionally, one or more selectable markers.

In a specific embodiment, a nucleic acid encoding an MDMIP polypeptide, or a portion thereof, is inserted into an expression vector. The expression vector is generated by subcloning the sequences into the EcoRl restriction site of each of the three available pGEX vectors (glutathione S-transferase expression vectors; see e.g., Smith et al., Gene 7:31–40, 1988), thus allowing the expression of products in the correct reading frame. Expression vectors that contain the sequences of interest may be identified by three general approaches: (i) nucleic acid hybridization, (ii) presence or absence of "marker" gene function and/or (iii) expression of the inserted sequences. In the first approach, MDMIP may be detected by nucleic acid hybridization using probes comprising sequences homologous and complementary to the inserted sequences of interest. In the second approach, the recombinant vector/host system may be identified and selected based upon the presence or absence of certain "marker" functions (e.g., binding to an antibody specific for the MDMIP polypeptide, resistance to antibiotics, occlusion-body formation in baculovirus, and the like) caused by the insertion of the sequences of interest into the vector.

Expression from certain promoters may be enhanced in the presence of certain inducer agents, thus facilitating control of the expression of the MDMIP polypeptide.

A host cell strain may be selected which modulates the expression of MDMIP sequences, or modifies/processes the expressed proteins in a desired manner. Moreover, different host cells possess characteristic and specific mechanisms for the translational and post-translational processing and modification (e.g., glycosylation, phosphorylation, and the like) of expressed proteins. Appropriate cell lines or host systems may thus be chosen to ensure the desired modification and processing of the foreign protein is achieved. For example, protein expression within a bacterial system can be used to produce an unglycosylated core protein; whereas expression within mammalian cells ensures "native" glycosylation of a heterologous protein.

A MDMIP nucleic acid can be engineered so that it encodes a fusion polypeptide having a portion of the MDMIP polypeptide, e.g., linked to a second polypeptide that includes a sequence that is derived from a polypeptide other than an MDMIP polypeptide. The second polypeptide can include, e.g., a marker polypeptide or fusion partner. For example, the polypeptide can be fused to a hexa-histidine tag to facilitate purification of bacterially expressed protein or a hemagglutinin tag to facilitate purification of protein expressed in eukaryotic cells.

Also included in the invention is a method of making an MDMIP polypeptide, e.g., a rat or human MDMIP polypeptide, by providing a cell containing DNA encoding an MDMIP polypeptide and culturing the cell under conditions permitting expression of the MDMIP encoding DNA, i.e., production of the recombinant MDMIP by the cell.

Various regions of the MDMIP nucleic acid can be used to detect MDMIP nucleic acids in populations of nucleic acids. For example, probes derived from nucleic acids 1–222 (SEQ ID NO:1), nucleic acids 1–486 of (SEQ ID NO:7) or nucleic acids 223–486 (SEQ ID NO:8) can be used to identify MDMIP nucleic acids. The probes can be, e.g., hybridization probes derived from these sequences, or primers which specifically amplify these sequences in amplification assays (such as PCR amplification assays).

MDMIP Polypeptides

Also provided in the invention is an MDMIP polypeptide, as well as variants and fragments of an MDMIP polypeptide. Preferably, the MDMIP polypeptide, variant or fragment binds an MDM2-polypeptide, e.g, it includes the amino acid sequence of SEQ ID NO:2.

In some embodiments, the MDMIP polypeptide is purified. A "purified" polypeptide, protein or biologically active portion thereof is substantially free of cellular material or other contaminating proteins from the cell or tissue source from which the MDMIP protein is derived, or substantially free from chemical precursors or other chemicals when chemically synthesized. The language "substantially free of cellular material" includes preparations of MDMIP protein in which the protein is separated from cellular components of the cells from which it is isolated or recombinantly produced. In one embodiment, the language "substantially free of cellular material" includes preparations of MDMIP protein having less than about 30% (by dry weight) of non-MDMIP protein (also referred to herein as a "contaminating protein"), more preferably less than about 20% of non-MDMIP protein, still more preferably less than about 10% of non-MDMIP protein, and most preferably less than about 5% non-MDMIP protein. When the MDMIP protein or biologically active portion thereof is recombinantly produced, it is also preferably substantially free of culture medium, i.e., culture medium represents less than about 20%, more preferably less than about 10%, and most preferably less than about 5% of the volume of the protein preparation.

In some embodiments, the MDMIP polypeptide, variant, or fragment binds an MDM2 polypeptide. In some embodiments, the MDMIP polypeptide includes an amino acid sequence at least 80% identical to a polypeptide which includes the amino acid sequence of SEQ ID NO:2. More preferably, the polypeptide is at least 85, 90, 95, 98, or even 99% or more identical. The percent relatedness of two amino acid sequences can be determined as described above for MDMIP nucleic acids.

The MDMIP polypeptides can be made by expressing MDMIP nucleic acids as described above and recovering the MDMIP polypeptide. Alternatively, the MDMIP polypeptide can be chemically synthesized using standard techniques, e.g., by the methods described in Solid Phase Peptide Synthesis, 2nd ed., 1984 The Pierce Chemical Co., Rockford, Ill.

The MDMIP polypeptide can be used to detect an MDM2 polypeptide in a biological sample by biological sample, e.g., a cell or tissue sample from a subject, or a cell population cultured in vitro. The sample is contacted with an MDMIP polypeptide under conditions sufficient to allow for formation of an MDM2-MDMIP complex (as explained below), if the MDM2 polypeptide is present in the sample and then detecting the complex. Presence of the MDMIP-MDM2 complex indicates the MDM2 polypeptide is present in the sample.

The MDMIP polypeptide can also be used to remove, or purify, an MDM2 polypeptide from a biological sample. The method includes contacting the sample with an MDMIP polypeptide under conditions sufficient to allow for formation of an MDM2-MDMIP complex; if the MDM2 polypeptide is present in the sample, and removing the complex from said sample, thereby removing said MDM2 polypeptide from said sample.

Preferably, the MDMIP polypeptide is labeled to facilitate detection and recovery of MDMIP-polypeptide complexes.

MDMIP Binding MDM2 Polypeptide Derivatives and Fragments

The invention also provides nucleic acids encoding polypeptides or peptides derived from an MDM2 polypeptide or peptide. Preferably, the nucleic acids encode polypeptides or peptides that contain an MDMIP binding domain. Also included in the invention are the polypeptides and peptides encoded by these nucleic acids.

In general, an MDMIP-binding MDM2 polypeptide according to the invention includes any region of an MDM2 polypeptide that is less than the length of a full-length MDM2 polypeptide, but which includes an MDMIP binding domain, e.g. is less than 491 amino acids and is greater than 4 amino acids in length. Preferably, the MDMIP-binding polypeptide is greater than 5, 6, 7, 8, 9, or 10 amino acids in length and is less than 25, 50, 75, 100, 150, 200, 250, 300, 350, 400 or 450 amino acids in length. The MDMIP-binding polypeptide preferably includes SEQ ID NO:4, or a related sequence.

By "MDM2 polypeptide" is meant a polypeptide at least 80% identical to the amino acid sequence of a polypeptide that includes an amino acid sequence of a human MDM2 polypeptide, e.g., the 491 amino acid polypeptide encoded by the nucleic acid sequence disclosed in GenBank Accession No. M92424.

By "MDMIP-binding domain" or "MDMIP-binding region" is meant a region of amino acids sufficient to allow the polypeptide in which the region of amino acids is present to bind specifically to an MDMIP polypeptide.

The MDMIP binding polypeptide present in the complex will typically include at least 6, 8, 10, 12, or 15 or more amino acids of an MDM2 polypeptide. Preferably, the polypeptide corresponds to a region of contiguous amino acids in a MDM2 polypeptide. In some embodiments, the MDM2 polypeptide is a polypeptide which includes the amino acid sequence encoded by SEQ ID NO:3 (i.e., nucleotides 312–921 of the nucleotide sequence represented by GenBank Accession Number M92424). The MDMIP binding polypeptide may be a full-length MDM2 polypeptide, e.g., it may have the amino acid sequence of the MDM2 polypeptide encoded by a human nucleic acid, which is available as GenBank Accession No. M92424.

Alternatively, the MDMIP binding MDM2 polypeptide includes a region of the amino acid sequence of SEQ ID NO:4 that is able to bind specifically to an MDMIP polypeptide. Procedures for identifying regions within SEQ ID NO:4 that bind to MDMIP can be readily identified by one of ordinary skill in the art and the procedures described herein. For example, nucleic acid sequences containing various portions of SEQ ID NO:3 can be tested in a yeast two hybrid screening assay in combination with a nucleic acid encoding the MDM2-binding region of an MDMIP polypeptide.

The invention also includes nucleic acids encoding MDMIP-binding fragments of an MDM2 polypeptide. The nucleic acids can include a nucleic acid sequence that is identical to a portion of a human MDM2 polypeptide disclosed in GenBank Accession No. M92424.

Alternatively, the nucleic acid can be an MDM2 variant that is greater than 70, 80, 85, 90, 95, 98, or even 99% identical to the corresponding region of the human MDM2 polypeptide nucleic acid. Alternatively, the nucleic acid encodes an MDMIP-binding MDM2 polypeptide which is greater than 70, 80, 85, 90, 95, 98, or even 99% identical to a portion of the human MDM2 polypeptide disclosed in GenBank Accession No. M92424.

Alternatively, the nucleic acid encoding an MDMIP-binding MDM2 polypeptide may hybridize under low, medium, or high stringency, using the parameters and conditions described above for MDMIP nucleic acids and polypeptides.

A MDMIP-binding MDM2 nucleic acid nucleic acid can be engineered so that it encodes a fusion polypeptide having a portion of the MDMIP polypeptide, e.g., linked to a second polypeptide that includes a sequence that is derived from a polypeptide other than an MDMIP polypeptide. The second polypeptide can include, e.g., a marker polypeptide or fusion partner. For example, the polypeptide can be fused to a hexa-histidine tag to facilitate purification of bacterially expressed protein or a hemagglutinin tag to facilitate purification of protein expressed in eukaryotic cells.

A nucleic acid encoding an MDMIP binding MDM2 peptide can be provided in vector as described above for vectors and cells containing MDMIP polypeptides. MDM2-binding MDMIP polypeptides can be synthesized by expressing nucleic acids encoding the MDMIP binding polypeptides and recovering the expressed polypeptides, e.g, using vectors and/or cells which include nucleic acid encoding an MDMIP binding MDM2 polypeptide.

Also included in the invention is a method of making an MDM2 polypeptide fragment, e.g., a rat or human MDMIP-binding MDM2 polypeptide fragment polypeptide, by providing a cell containing DNA encoding an MDMIP-binding MDM2 polypeptide fragment and culturing the cell under conditions permitting expression of the MDM2 fragment encoding DNA, i.e., production of the recombinant MDM2 polypeptide by the cell.

Chimeric Polypeptides Including an MDM2-binding Region of a MDMIP Polypeptide and an MDMIP Region of an MDM2 Polypeptide Also included in the invention is a chimeric polypeptide or peptide which includes a region of an MDM2 polypeptide covalently linked, e.g., via a peptide bond, to a region of an MDMIP polypeptide. In some embodiments, the chimeric polypeptide includes six or more amino acids of an MDM2 polypeptide covalently linked to six or more amino acids of an DMIP polypeptide.

Preferably, the MDM2 polypeptide in the chimeric polypeptide includes an MDMIP-binding domain. Preferably, the MDMIP polypeptide in the chimeric polypeptide includes an MDM2-binding polypeptide. In some embodiments, the MDM2 and MDMIP polypeptides of the chimeric polypeptide interact to form a complex. Any MDMIP polypeptide disclosed herein can be used in the complex, e.g., the chimeric polypeptide can include an amino acid sequence at least 90% identical to the amino acid sequence of SEQ ID NO:2. Similarly, any MDM2 polypeptide can be present in the chimeric polypeptide.

Also included in the invention are nucleic acids encoding the chimeric polypeptides or peptides, as well as vectors and cells containing these nucleic acids.

The chimeric polypeptides can be constructed by expressing nucleic acids encoding chimeric polypeptides using vectors and cells as described above for MDMIP polypeptides and MDM2 polypeptides, and then recovering the chimeric polypeptides, or by chemically synthesizing the chimeric polypeptides.

MDM2-MDMIP Complexes

In another aspect, the invention includes a purified complex that includes the MDM2-binding domain of an MDMIP polypeptide and an MDMIP-binding domain of a MDM2 polypeptide. By purified complex is meant a complex of polypeptide that includes an MDM2-binding domain of an MDMIP polypeptide and a polypeptide that includes and MDMIP binding domain of an MDM2 polypeptide.

In general, the complex can include any MDMIP polypeptide described herein as long as it includes an MDM2 binding domain. Similarly, any MDM2 polypeptide, or any MDM2 derived polypeptide, can be used as long as it contains an MDMIP binding region.

Thus, the MDM2-binding polypeptide and the MDMIP-binding polypeptide present in the complex can have the amino acid sequence of a mammalian MDMIP polypeptide, (e.g, mouse, rat, pig, cow, dog, monkey, frog), or of insects (e.g., fly), plants or, most preferably, human. In some embodiments, both polypeptides have the amino acid sequences of regions of the corresponding human polypeptides. For example, the complex can include a human MDM2 polypeptide, or an MDMIP binding fragment of a human MDM2 polypeptide, and a human MDMIP polypeptide, or a MDM2 -binding fragment of a human MDMIP polypeptide.

In various embodiments, other components, e.g., polypeptides, are present in the complex in addition to the MDM2-binding domain of an MDMIP polypeptide and the MDMIP binding domain of an MDM2 polypeptide. In some embodiments, one or more polypeptides, such as p53, Rb, E2F-1, DP1 and Numb are absent from the complex. In additional embodiments, MDMIP binding polypeptide and the MDM2-binding polypeptides are the only polypeptide components present in significant levels in the complex. An example of such a complex is a purified complex of a human MDM2 polypeptide and a human MDMIP polypeptide.

In some embodiments, the MDM2-binding polypeptide and the MDMIP binding polypeptide complex is a functionally active complex. As utilized herein, the term "functionally active MDM2-binding polypeptide and the MDMIP binding polypeptide complex" refers to species displaying one or more known functional attributes of a full-length MDM2 protein complexed with full-length MDMIP. These attributes include, e.g., the control of cellular and physiological processes, such as: (i) control of cell-cycle progression; (ii) cellular differentiation and apoptosis; (iii) regulation of transcription; and (iv) pathological processes including, e.g., hyperproliferative disorders (e.g., tumorigenesis and tumor progression).

In other embodiments, the complex is not functionally active i.e., the complex lacks one or more of these functional attributes.

Either, or both, of the MDMIP or MDM2-binding polypeptides in the complex may be labeled, i.e., attached to one or more detectable substances. Labeling can be performed using any art recognized method for labeling polypeptides. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

The complexes can be made by expressing each polypeptide from each nucleic acid and allowing the complex to form from the expressed polypeptides. Any of the nucleic acids disclosed herein that express MDM2-binding MDMIP polypeptides or MDMIP biding MDM2 polypeptides (or chimerics of these polypeptides) can be used, as can vectors and cells expressing these polypeptides. If desired, the complexes can then be recovered and isolated.

Once a recombinant cell expressing the MDM2 protein and/or MDMIP, or a fragment or derivative thereof, is identified, the individual gene product or complex may be isolated and analyzed. This is achieved by assays that are based upon the physical and/or functional properties of the protein or complex. The assays can include, e.g., radioactive labeling of one or more of the polypeptide complex components, followed by analysis by gel electrophoresis, immunoassay, cross-linking to marker-labeled products. The MDM2 protein-MDMIP complex may be isolated and purified by standard methods known in the art (either from natural sources or recombinant host cells expressing the proteins/protein complex). These methods can include, e.g., column chromatography (e.g., ion exchange, affinity, gel exclusion, reverse-phase, high pressure, fast protein liquid, etc), differential centrifugation, differential solubility, or similar methods used for the purification of proteins.

The MDM2 protein-MDMIP complex is implicated in the modulation of functional activities of the MDM2 protein. Such functional activities include, e.g., (i) control of cell-cycle progression; (ii) cellular differentiation and apoptosis; (iii) regulation of transcription; and (iv) pathological processes including, but not restricted to, hyperproliferative disorders (e.g., tumorigenesis and tumor progression).

The MDM2 protein-MDMIP complex may be analyzed by hydrophilicity analysis (see e.g., Hopp & Woods, Proc. Natl. Acad. Sci. USA 78:3824–3828, 1981). This analysis can be used to identify the hydrophobic and hydrophilic regions of the proteins, thus aiding in the design of substrates for experimental manipulation, such as in binding experiments, antibody synthesis. Secondary structural analysis may also be performed to identify regions of the MDM2 protein and/or MDMIP which assume specific structural motifs. See e.g., Chou & Fasman, Biochem. 13:222–223, 1974. Manipulation, translation, secondary structure prediction, hydrophilicity and hydrophobicity profiles, open reading frame prediction and plotting, and determination of sequence homologies, can be accomplished using computer software programs available in the art.

Other methods of structural analysis, e.g., X-ray crystallography (see e.g., Engstrom, Biochem. Exp. Biol. 11:7–13, 1974); mass spectroscopy and gas chromatography (see e.g., Methods in Protein Science, J. Wiley and Sons, New York, N.Y., 1997) and computer modeling (see e.g., Fletterick & Zoller, eds., Computer Graphics and Molecular Modeling, In: *Current Communications in Molecular Biology*, Cold Spring Harbor Laboratory Press, Cold Spring Harbor, N.Y., 1986) may also be used to characterize complexes.

Antibodies to MDMIP Polypeptides, MDMIP Binding Polypeptides of MDM2 Polypeptides, and Complexes of MDMIP Polypeptides and MDM2 Polypeptides The invention further encompasses antibodies and antibody fragments (such as Fab or (Fab)2 fragments) that bind specifically to any of the polypeptides or complexes described herein. By "specifically binds" is meant an antibody that recognizes and binds to a particular antigen, e.g., an MDMIP polypeptide of the invention, but which does not substantially recognize or bind to other molecules in a sample, e.g., a biological sample, which includes an MDMIP polypeptide.

These polypeptides and complexes can include, e.g., an MDMIP polypeptide, an MDMIP binding MDM2 polypeptide, a chimeric MDM2-MDMIP polypeptide, or a complex of an MDMIP polypeptide and MDM2 polypeptide. The antibodies and antibody fragments can alternatively be raised against variants or fragments of the complexes or polypeptides. For example, a purified MDMIP polypeptide, or a portion, variant, or fragment thereof, can be used as an immunogen to generate antibodies that bind MDMIP using standard techniques for polyclonal and monoclonal antibody preparation.

A full-length MDMIP polypeptide can be used, if desired. Alternatively, the invention provides antigenic peptide fragments of MDMIP polypeptides for use as immunogens. In some embodiments, an antigenic MDMIP peptide includes at least four amino acid residues of the amino acid sequence shown in SEQ ID NO:2. The antigenic peptide encompasses an epitope of MDMIP such that an antibody raised against the peptide forms a specific immune complex with MDMIP. In some embodiments, the antigenic peptide includes at least 6, 8, 10, 15, 20, or 30 or more amino acid residues of an MDMIP polypeptide. In one embodiment, epitopes encompassed by the antigenic peptide are regions of MDMIP that bind MDM2, or are located on he surface of the protein, e.g., hydrophilic regions.

In some embodiments, the antibodies are raised against an MDMIP-MDM2 complex. Preferably, the anti-complex antibodies bind with higher affinity to the complex as compared to their affinity for an isolated MDM2 polypeptide or an isolated MDMIP polypeptide.

If desired, peptides containing antigenic regions can be selected using hydropathy plots showing regions of hydrophilicity and hydrophobicity. These plots may be generated by any method well known in the art, including, for example, the Kyte Doolittle or the Hopp Woods methods, either with or without Fourier transformation. See, e.g., Hopp and Woods, Proc. Nat. Acad. Sci. USA 78:3824–3828, 1981; Kyte and Doolittle, J. Mol. Biol. 157:105–142, 1982, each incorporated herein by reference in their entirety.

The MDMIP polypeptide sequence of SEQ ID NO:2, or derivatives, fragments, analogs or homologs thereof, may be utilized as immunogens in the generation of antibodies that specifically bind these protein components. The term "antibody" as used herein refers to immunoglobulin molecules and immunologically active portions of immunoglobulin molecules, i.e., molecules that contain an antigen binding site that specifically binds (immunoreacts with) an antigen, such as MDMIP, an MDMIP binding polypeptide fragment of MDM2, or a complex including the two polypeptides. Such antibodies include, e.g., polyclonal, monoclonal, chimeric, single chain, $F_{ab}$ and $F_{(ab')2}$ fragments, and an $F_{ab}$ expression library. In specific embodiments, antibodies to human MDMIP polypeptides or complexes of human MDMIP and MDM2 polypeptides are disclosed.

Various procedures known within the art may be used for the production of polyclonal or monoclonal antibodies. For example, for the production of polyclonal antibodies, various suitable host animals (e.g., rabbit, goat, mouse or other mammal) may be immunized by injection with the native protein, or a synthetic variant thereof, or a derivative of the foregoing. An appropriate immunogenic preparation can contain, for example, recombinantly expressed MDMIP, MDM2, or chimeric polypeptide including the two polypeptides, or a complex including the two polypeptides. Alternatively, the immunogenic polypeptide or polypeptides may be chemically synthesized.

The preparation can further include an adjuvant. Various adjuvants used to increase the immunological response include, e.g., Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as Bacille Calmette-Guerin and *Corynebacterium parvum*, or similar immunostimulatory agents. If desired, the antibody molecules directed against MDMIP, MDM2, chimeras, or complexes can be isolated from the mammal (e.g., from the blood) and further purified by well known techniques, such as protein A chromatography to obtain the IgG fraction.

The term "monoclonal antibody" or "monoclonal antibody composition", as used herein, refers to a population of antibody molecules that contain only one species of an antigen binding site capable of immunoreacting with a particular epitope MDMIP, MDM2, chimeras, or complex of these polypeptides. A monoclonal antibody composition thus typically displays a single binding affinity for a particular protein with which it immunoreacts. For preparation of monoclonal antibodies directed towards a particular MDMIP polypeptide, MDM2 polypeptide, chimeras, or complex, or derivatives, fragments, analogs or homologs thereof, any technique that provides for the production of antibody molecules by continuous cell line culture may be utilized. Such techniques include, e.g., the hybridoma technique (see Kohler & Milstein, Nature 256:495–497, 1975); the trioma technique; the human B-cell hybridoma technique (see Kozbor, et al., Immunol Today 4:72, 1983) and the EBV hybridoma technique to produce human monoclonal antibodies (see Cole, et al., In: *Monoclonal Antibodies and Cancer Therapy*, Alan R. Liss, Inc., 1985, pp. 77–96). If desired, human monoclonal antibodies may be prepared by using human hybridomas (see Cote, et al., Proc. Natl. Acad. Sci. USA 80:2026–2030, 1983) or by transforming human B-cells with Epstein Barr Virus in vitro (see Cole, et al., In: *Monoclonal Antibodies and Cancer Therapy*, supra). Each of the above citations are incorporated herein by reference in their entirety.

Techniques can be adapted for the production of single-chain antibodies specific to a MDMIP polypeptide, MDMIP-binding MDM2 polypeptide (or fragment), MDM2-MDMIP chimeric polypeptide, or a complex of an MDMIP and MDM2 polypeptide (see e.g., U.S. Pat. No. 4,946,778). In addition, methods can be adapted for the construction of $F_{ab}$ expression libraries (see e.g., Huse, et al., Science 246:1275–1281, 1989) to allow rapid and effective identification of monoclonal $F_{ab}$ fragments with the desired specificity for the desired protein or derivatives, fragments, analogs or homologs thereof. Non-human antibodies can be "humanized" by techniques well known in the art. See e.g., U.S. Pat. No. 5,225,539. Each of the above citations is incorporated herein by reference. Antibody fragments that contain the idiotypes to a MDMIP protein may be produced by techniques known in the art including, e.g.: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Additionally, recombinant anti-MDMIP polypeptide, MDMIP binding MDM2 polypeptide (or fragment), MDM2-MDMIP chimeric polypeptide, a complex of an MDMIP and MDM2 polypeptide antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al., Science 240:1041–1043, 1988; Liu et al., Proc. Nat. Acad. Sci. USA 84:3439–3443, 1987; Liu et al., J. Immunol. 15 139:3521–3526, 1987; Sun et al., Proc. Nat. Acad. Sci. USA 84:214–218, 1987; Nishimura et al., Cancer Res. 47:999–1005, 1987; Wood et al., Nature 314:446–449, 1985; Shaw et al., J. Natl. Cancer Inst. 80:1553–1559, 1988; Morrison, Science 229:1202–1207, 1985; Oi et al., BioTechniques 4:214, 1986; U.S. Pat. No. 5,225,539; Jones et al., Nature 321:552–525, 1986; Verhoeyan et al., Science 239:1534, 1988; and Beidler et al., J. Immunol. 141:4053–4060, 1988. Each of the above citations is incorporated herein by reference.

In one embodiment, methods for the screening of antibodies that possess the desired specificity include, e.g., enzyme-linked immunosorbent assay (ELISA) and other immunologically-mediated techniques known within the art. In a specific embodiment, selection of antibodies that are specific to a particular domain of a MDMIP polypeptide, MDMIP binding MDM2 polypeptide (or fragment), MDM2-MDMIP chimeric polypeptide, or a complex of an MDMIP and MDM2 polypeptide is facilitated by generation of hybridomas that bind to the fragment of a polypeptide or complex possessing such a domain. Antibodies that are specific for one or more domains within a given polypeptide or complex, e.g., the domain including the amino acids of SEQ ID NO:2 in a MDMIP polypeptide, or derivatives, fragments, analogs or homologs thereof, are also provided herein.

An anti-MDMIP polypeptide, MDMIP binding MDM2 polypeptide (or fragment), MDM2-MDMIP chimeric polypeptide, or a complex of an MDMIP and MDM2 polypeptide antibodies may be used in methods known within the art relating to the localization and/or quantitation of a given polypeptide or complex (e.g., for use in measuring levels of the given polypeptide complex within appropriate physiological samples, for use in diagnostic methods, for use in imaging the protein, and the like). In one embodiment, antibodies for the given polypeptide or complex, or derivatives, fragments, analogs or homologs thereof, that contain the antibody derived binding domain, are utilized as pharmacologically-active compounds.

An anti-MDMIP polypeptide, MDMIP binding MDM2 polypeptide (or fragment), MDM2-MDMIP chimeric polypeptide, or an anti-MDMIP-MDM2 complex of an MDMIP and MDM2 polypeptide antibody (e.g., monoclonal antibody) can be used to isolate MDMIP, MDM2 polypeptides, or complexes including MDMIP polypeptides and MDM2 polypeptides, by standard techniques, such as affinity chromatography or immunoprecipitation. Thus, the anti-antibodies disclosed herein can facilitate the purification of complexes of MDM2 and MDMIP polypeptides from cells and of recombinantly produced MDM2 and MDMIP polypeptides expressed in host cells.

An antibody of the invention can additionally be used to detect MDM2, MDMIP polypeptides, or complexes of MDMIP and MDM2 polypeptides (e.g., in a cellular lysate or cell supernatant) in order to evaluate the abundance and pattern of expression of these polypeptides or complexes. Further, the herein disclosed antibodies can be used diagnostically to monitor protein levels in tissue as part of a clinical testing procedure, e.g., to, for example, determine the efficacy of a given treatment regimen. Detection can be facilitated by coupling (ie., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Use of MDM2 Protein-MDMIP Complexes or Their Component Polypeptides to Identify MDMIP and MDM2 Interacting Agents The MDMIP, MDM2, and complexes disclosed herein can also be used to identify compounds or other agents which modulate the activity of MDM2 and/or MDMIP-mediated process. For example, to identify an agent that modulates MDM2 or MDMIP activity, an MDMIP-MDM2 complex is tested with a test agent and binding of the agent to the complex is measured. Binding of the agent to the complex indicates the agent modulates MDM2 or MDMIP polypeptide activity.

Any compound or other molecule (or mixture or aggregate thereof) can be used as a test compound. In some embodiments, the agent can be a small peptide, or other small molecule produced by e.g., combinatorial synthetic methods known in the art. Binding of the compound to the complex can be determined using art recognized methods, e.g., by immunoprecipitation using antibodies (e.g., antibodies against MDMIP, MDM2, or the MDM2IP-MDM2 complex). Bound agents can be identified by comparing the relative electophoretic mobility of complexes exposed to the test agent to the mobility of complexes that have not been exposed to the test agent. Altered migration of the test complexes indicates the test agent binds to the MDMIP-MDM2 complex.

Also provided for in the invention is a method for identifying agents which modulate MDMIP activity by contacting an MDMIP polypeptide (or an MDMIP-binding fragment of an MDM2 polypeptide) with a test agent, and measuring binding of the agent to the complex. Binding of the agent to the complex indicates the agent modulates MDMIP polypeptide activity. As described above, any art-recognized method for determining binding of a compound to a test compound can be used.

Agents identified in the screening assays can be further tested for their ability to alter and/or modulate cellular functions, particularly those functions in which the MDM2 protein has been implicated. These functions include, e.g., control of cell-cycle progression; regulation of transcription; control of intracellular signal transduction; and pathological processes, as well as various other biological activities (e.g., binding to an anti-MDM2 protein•MDMIP complex antibody).

Methods of Diagnosing Conditions Associated with Altered Levels of MDMIP Polypeptides or MDM2-MDMIP Polypeptide Complexes MDM2 is implicated in multiple biological processes. Accordingly, a variety of conditions can be or identified in subjects by measuring the levels of MDM2-MDMIP complexes in a subject and comparing the levels of the MDM2-

MDMIP complexes to the levels of the complexes in a reference population whose corresponding status with respect to the compared condition is known.

Comparable levels of the MDM2-MDMIP complex in the test sample and the reference sample indicates the subject has the MDM2-MDMIP complex associated disorder (or absence thereof) as that of the reference population. In contrast, altered levels of the complex in the test and reference populations indicates the subject's status with respect to the MDM-MDMIP disorder is different from that in the control population. Thus, if the reference cell population includes cells from individuals that do not have the MDM2-MDMIP associated disorder, a similarity in MDMIP-MDM2 complex levels in the test and control populations indicates the subject does not have the MDMIP-MDM2 complex-associated disorder. Conversely, a difference in the levels of the test and reference populations indicates the subject has, or has a predisposition to, the MDM2-MDMIP disorder.

In general, a test cell population from the subject includes at least one cell that is capable of expressing genes encoding the polypeptide, or polypeptides making up the measured complex (i.e., the cell expresses an MDMIP polypeptide, MDM2, polypeptide, or both). By "capable of expressing" is meant that the corresponding gene or genes is present in an intact form in the cell and can be expressed.

In general, any reference cell population can be used, as long as its status with respect to the measure parameter is known (i.e., the reference cell population is known to possess or lack the property or trait being measured in the test cell population), and whose level of MDMIP-MDM2 complex is known. In some embodiments, the reference cell population is made up substantially, or preferably exclusively, of such cells whose status is known.

Preferably, cells in the reference cell population are derived from a tissue type as similar as possible to a test cell. In some embodiments, the control cell is derived from the same subject as the test cell. In other embodiments, the control cell population is derived from a database of molecular information derived from cells for which the assayed parameter or condition is known. The subject is preferably a mammal. The mammal can be, e.g, a human, non-human primate, mouse, rat, dog, cat, horse, or cow.

In some embodiments, the reference cell population is derived from a plurality of cells. For example, the reference cell population can be a database of expression patterns from previously tested cells for which one of the herein-described parameters or conditions is known. If desired, comparison of differentially expressed sequences between a test cell population and a reference cell population can be done with respect to a expression of a control gene whose expression is independent of the parameter or condition being measured. Expression levels of the control nucleic acid in the test and reference nucleic acid can be used to normalize signal levels in the compared populations.

In some embodiments, the test cell population is compared to multiple reference cell populations. Each of the multiple reference populations may differ in the known parameter. Thus, a test cell population may be compared to a second reference cell population known to contain, e.g., tumorous cells, as well as a second reference population known to contain, e.g., non-tumorous cells.

The test cell or cell population in any of the herein described diagnostic or screening assays can be taken from a known or suspected tumor containing sample or from a bodily fluid, e.g, biological fluid (such as blood, serum, urine, saliva, milk, ductal fluid, or tears). For many applications, cells present in a bodily fluid can be examined instead of a primary lesion. Thus, the need for taking a biopsy from a known or suspected primary tumor site is obviated.

In another aspect, disorders associated with altered levels of MDMIP or MDM2-MDMIP complexes are identified in a subject by measuring expression of MDMIP nucleic acids. Expression of MDMIP sequences can be detected (if present) and measured using techniques well known to one of ordinary skill in the art. For example, sequences disclosed herein (e.g. SEQ ID NO:1) can be used to construct probes for detecting MDMIP RNA sequences in, e.g., northern blot hybridization analyses. As another example, the sequences can be used to construct primers for specifically amplifying sequences in, e.g, amplification-based detection methods such as reverse-transcription based polymerase chain reaction.

Expression level of MDMIP sequences in the test cell population is then compared to expression levels of the sequences in one or more cells from a reference cell population. Expression of the genes disclosed herein can be measured at the RNA level using any method known in the art. For example, northern hybridization analysis using probes which specifically recognize one or more of these sequences can be used to determine gene expression. Alternatively, expression can be measured using reverse-transcription-based PCR assays, e.g., using primers specific for the differentially expressed sequences. When alterations in gene expression are associated with gene amplification or deletion, sequence comparisons in test and reference populations can be made by comparing relative amounts of the examined DNA sequences in the test and reference cell populations.

Levels of MDM2 protein-MDMIP complexes can be used to determine the presence of, or predisposition to, multiple states in a subject. For example, these complexes can serve as markers for specific disease states that involve the disruption of physiological processes. These processes can include e.g., control of cell-cycle progression, cellular differentiation and apoptosis, or regulation of transcription. In addition, a subject can be assessed for the presence, or predisposition to, pathological processes. These processes can include, e.g., hyperproliferative disorders (e.g., tumorigenesis and tumor progression).

In addition to diagnostic methods, the herein described methods can be used to assess the prognosis, or follow the course of, a disease or condition associated with altered levels of MDMIP-MDM2 complexes (or its components) in a subject. These methods can additionally b use to determine the efficacy of administered therapeutics.

To detect MDMIP-MDM2 complexes, the herein disclosed antibodies may be used. For example, anti MDMIP-MDM2 complex antibodies or anti-MDMIP antibodies can be used in assays (e.g., immunoassays) to detect, prognose, diagnose, or monitor various conditions, diseases, and disorders characterized by aberrant levels of MDM2 protein-MDMIP complex. They can alternatively used to monitor the treatment of conditions associated with altered levels of these complexes, or their components thereof.

To perform immunoassays using antibodies for MDMIP-MDM2 complexes, a sample derived from a patient is contacted with an anti-MDM2 protein-MDMIP complex antibody under conditions such that specific binding may occur. Specific binding by the antibody is then detected, if present, and quantitated.

In a specific embodiment, an antibody specific for a MDM2 protein-MDMIP complex is used to analyze a tissue or serum sample from a patient for the presence of MDM2 protein-MDMIP complex. An aberrant level of MDM2 protein-MDMIP complex is indicative of a diseased condition. The immunoassays which may be utilized include, e.g., competitive and non-competitive assay systems using techniques such as Western Blots, radioimmunoassays (RIA), enzyme linked immunosorbent assay (ELISA), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein-A immunoassays.

In some embodiments, diseases and disorders involving or characterized by aberrant levels of MDM2 protein-MDMIP complex or a predisposition to develop such disorders may be diagnosed by detecting aberrant levels of MDM2 protein-MDMIP complex, or non-complexed MDM2 protein and/or MDMIP proteins or nucleic acids for functional activity. Suitable functional activities that can be assayed include, e.g., (i) binding to an interacting partner (e.g., the MDM2 protein, MDMIP) or (ii) by detecting mutations in MDM2 protein and/or a MDMIP RNA, DNA or protein (e.g., translocations, truncations, changes in nucleotide or amino acid sequence relative to wild-type MDM2 protein and/or the MDMIP) which can cause increased or decreased expression or activity of the MDM2 protein, a MDMIP or a MDM2 protein-MDMIP complex.

Methods which are well-known within the art (e.g., immunoassays, nucleic acid hybridization assays, biological activity assays, and the like) may be used to determine whether one or more particular MDM2 protein-MDMIP complexes are present at either increased or decreased levels, or are absent, within samples derived from patients suffering from a particular disease or disorder, or possessing a predisposition to develop such a disease or disorder, as compared to the levels in samples from subjects not having such disease or disorder or predisposition thereto. Additionally, these assays may be utilized to determine whether the ratio of the MDM2 protein-MDMIP complex to the non-complexed components (i.e. the MDM2 protein and/or the specific MDMIP) in the complex of interest is increased or decreased in samples from patients suffering from a particular disease or disorder or having a predisposition to develop such a disease or disorder as compared to the ratio in samples from subjects not having such a disease or disorder or predisposition thereto.

Accordingly, in specific embodiments of the present invention, diseases and disorders which involve increased/decreased levels of one or more MDM2 protein-MDMIP complex may be diagnosed, or their suspected presence may be screened for, or a predisposition to develop such diseases and disorders may be detected, by quantitatively ascertaining increased/decreased levels of: (i) the one or more MDM2 protein-MDMIP complex; (ii) the mRNA encoding both protein members of the complex; (iii) the complex functional activity or (iv) mutations in the MDM2 protein or the MDMIP (e.g., translocations in nucleic acids, truncations in the gene or protein, changes in nucleotide or amino acid sequence relative to wild-type MDM2 protein or the MDMIP) which enhance/inhibit or stabilize/destabilize MDM2 protein-MDMIP complex formation.

Antibodies directed against the MDM2 protein-MDMIP complex can also be used to detect cells which express the protein or protein complexes. Using such assays, specific cell types may be quantitatively characterized in which one or more particular MDM2 protein-MDMIP complex are expressed, and the presence of the component polypeptides or protein complex may be correlated with cell viability by techniques well-known within the art (e.g., florescence-activated cell sorting).

In some embodiments, expression is detected in in vitro cell culture models which express particular MDM2 protein-MDMIP complex, or derivatives thereof, for the purpose of characterizing and/or isolating MDM2 protein-MDMIP complex. These detection techniques include, e.g., cell-sorting of prokaryotes (see e.g., Davey & Kell, 1996. *Microbiol. Rev.* 60:641–696); primary cultures and tissue specimens from eukaryotes, including mammalian species such as human (see e.g., Steele, et al., 1996. *Clin. Obstet. Gynecol* 39:801–813) and continuous cell cultures (see e.g., Orfao & Ruiz-Arguelles, 1996. *Clin. Biochem.* 29:5–9.

The observation that MDMIP interacts with MDM2 polypeptide can also be used to detect the presence of, and, if desired, to purify, the binding polypeptides in a biological sample. For example, levels of MDM2 polypeptide in a biological sample can also be measured by contacting the sample with a labeled polypeptide including the MDM2-binding domain of an MDMIP polypeptide. Similarly, the presence of MDMIP in a biological sample can be measured by contacting the sample with a polypeptide that includes an MDMIP binding region or domain of an MDM2 polypeptide.

Kits Containing Reagents for Identifying MDMIP-MDM2 Complexes and MDM-IP Nucleic Acids The invention additionally provides kits for diagnostic use. The kits include one or more containers containing an anti-MDM2 protein-MDMIP complex antibody and, optionally, a labeled binding partner to the antibody. The label incorporated into the anti-MDM2 protein-MDMIP complex antibody may include, e.g., a chemiluminescent, enzymatic, fluorescent, colorimetric or radioactive moiety. Alternatively, the kit may include, in one or more containers, a pair of oligonucleotide primers (e.g., each 6–30 nucleotides in length) which are capable of acting as amplification primers for: polymerase chain reaction (PCR; see e.g., Innis, et al., 1990. PCR Protocols [Academic Press, Inc., San Diego, Calif.]), ligase chain reaction, cyclic probe reaction, or other methods known within the art. The kit may, optionally, further comprise a predetermined amount of a purified MDM2 protein, MDMIP or MDM2-MDMIP complex, or nucleic acids thereof, for use as a standard or control in the aforementioned assays.

Transgenic Animals

The host cells of the invention can also be used to produce nonhuman transgenic animals. For example, in one embodiment, a host cell of the invention is a fertilized oocyte or an embryonic stem cell into which MDMIP-coding sequences have been introduced. Such host cells can then be used to create non-human transgenic animals in which exogenous MDMIP sequences have been introduced into their genome or homologous recombinant animals in which endogenous MDMIP sequences have been altered. Such animals are useful for studying the function and/or activity of MDMIP and for identifying and/or evaluating modulators of MDMIP activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous MDMIP gene has been altered by homologous recombination between the endogenous gene and an exogenous DNA molecule introduced into a cell of the animal, e.g., an embryonic cell of the animal, prior to development of the animal.

A transgenic animal of the invention can be created by introducing MDMIP-encoding nucleic acid into the male pronuclei of a fertilized oocyte, e.g., by microinjection, retroviral infection, and allowing the oocyte to develop in a pseudopregnant female foster animal. The human MDMIP DNA sequence of SEQ ID NO:1 can be introduced as a transgene into the genome of a non-human animal. Alternatively, a nonhuman homologue of the human MDMIP gene, such as a mouse MDMIP gene, can be isolated based on hybridization to the human MDMIP cDNA (described further above) and used as a transgene. Intronic sequences and polyadenylation signals can also be included in the transgene to increase the efficiency of expression of the transgene. A tissue-specific regulatory sequence(s) can be operably linked to the MDMIP transgene to direct expression of MDMIP protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan In: *Manipulating the Mouse Embryo*, Cold Spring Harbor Laboratory Press, Cold Spring Harbor, N.Y. 1986. Similar methods are used for production of other transgenic animals. A transgenic founder animal can be identified based upon the presence of the MDMIP transgene in its genome and/or expression of MDMIP mRNA in tissues or cells of the animals. A transgenic founder animal can then be used to breed additional animals carrying the transgene. Moreover, transgenic animals carrying a transgene encoding MDMIP can further be bred to other transgenic animals carrying other transgenes.

To create a homologous recombinant animal, a vector is prepared which contains at least a portion of a MDMIP gene into which a deletion, addition or substitution has been introduced to thereby alter, e.g., functionally disrupt, the MDMIP gene. The MDMIP gene can be a human gene (e.g., a sequence including SEQ ID NO:1), but more preferably, is a non-human homologue of a human MDMIP gene. For example, a mouse homologue of human MDMIP gene of SEQ ID NO:1 can be used to construct a homologous recombination vector suitable for altering an endogenous MDMIP gene in the mouse genome. In one embodiment, the vector is designed such that, upon homologous recombination, the endogenous MDMIP gene is functionally disrupted (i.e., no longer encodes a functional protein; also referred to as a "knock out" vector).

Alternatively, the vector can be designed such that, upon homologous recombination, the endogenous MDMIP gene is mutated or otherwise altered but still encodes functional protein (e.g., the upstream regulatory region can be altered to thereby alter the expression of the endogenous MDMIP protein). In the homologous recombination vector, the altered portion of the MDMIP gene is flanked at its 5' and 3' ends by additional nucleic acid of the MDMIP gene to allow for homologous recombination to occur between the exogenous MDMIP gene carried by the vector and an endogenous MDMIP gene in an embryonic stem cell. The additional flanking MDMIP nucleic acid is of sufficient length for successful homologous recombination with the endogenous gene. Typically, several kilobases of flanking DNA (both at the 5' and 3' ends) are included in the vector. See e.g., Thomas et al., *Cell* 51:503, 1987, for a description of homologous recombination vectors. The vector is introduced into an embryonic stem cell line (e.g., by electroporation) and cells in which the introduced MDMIP gene has homologously recombined with the endogenous MDMIP gene are selected (see e.g., Li et al., *Cell* 69:915, 1992).

The selected cells are then injected into a blastocyst of an animal (e.g., a mouse) to form aggregation chimeras. See e.g., Bradley, In: *Teratocarcinomas and Embryonic Stem Cells: A Practical Approach*, Robertson, ed. IRL, Oxford, 1987, pp. 113–152. A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, Curr. Opin. Biotechnol. 2:823–829, 1991; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, see, e.g., Lakso et al., Proc. Nat. Acad. Sci. USA 89:6232–6236, 1992. Another example of a recombinase system is the FLP recombinase system of *Saccharomyces cerevisiae* (O'Gorman et al., Science 251:1351–1355, 1991. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al., Nature 385:810–813, 1997. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

Alternatively, transgenic animals can be prepared as above using nucleotide sequences encoding an MDMIP-binding fragment of an MDM2 protein or an MDM2 protein-MDMIP chimeric polypeptide.

Therapeutic Uses of MDMIP Polypeptides, MDMIP Binding MDM2 Polypeptides, and MDM2 Protein-MDMIP Complexes The MDM2 protein has been implicated to play a significant role in disorders of cell-cycle progression, cell differentiation, and transcriptional control, including cancer and tumorigenesis.

Based in part on the discovery of the MDMIP polypeptide, the invention provides for treatment or prevention of various diseases and disorders by administration of a biologically-active, therapeutic compound (hereinafter "Therapeutic"). Such Therapeutics include, e.g.,: (i) various MDM2 protein•MDMIP complexes (e.g., the MDM2 protein complexed with MDMIP) and derivative, fragments, analogs and homologs thereof; (ii) antibodies directed against these proteins and protein complexes; (iii) nucleic acids encoding the MDM2 protein and MDMIP and derivatives, fragments, analogs and homologs thereof; (iv) antisense nucleic acids encoding the MDM2 protein and (v) MDM2 protein IPs and MDM2 protein•MDMIP complex and modulators (i.e., inhibitors, agonists and antagonists) thereof (i) Disorders with Increased MDM2 protein and MDM2 protein•MDMIP Complex Levels Diseases and disorders which are characterized by increased (relative to a subject not suffering from the disease or disorder) MDM2 protein-MDMIP levels or biological activity may be treated with Therapeutics which antagonize (i.e., reduce or inhibit) MDM2 protein-MDMIP complex formation or activity. Therapeutics which antagonize MDM2 protein-MDMIP complex formation or activity may be administered in a therapeutic or prophylactic manner. Therapeutics which may be utilized include, e.g., the MDM2 protein or MDMIP, or analogs, derivatives, fragments or homologs thereof; (ii) anti-MDM2 protein-MDMIP complex antibodies; (iii) nucleic acids encoding the MDM2 protein or MDMIP; (iv) concurrent administration of a MDM2 protein and a MDMIP antisense nucleic acid and MDM2 protein and/or MDMIP nucleic acids which are "dysfunctional" (i.e., due to a heterologous [non-MDM2 protein and/or non-MDMIP] insertion within the coding sequences of the MDM2 protein and MDMIP coding sequences) are utilized to "knockout" endogenous MDM2 protein and/or MDMIP function by homologous recombination (see e.g., Capecchi, Science 244:1288–1292, 1989). Alternatively, mutants or derivatives of a first MDMIP which possess greater affinity for MDM2 protein than the wild-type first MDMIP may be administered to compete with a second MDMIP for binding to the MDM2 protein, thereby reducing the levels of complex between the MDM2 protein and the second MDMIP.

Increased levels of MDM2 protein-MDMIP complex can be readily detected by quantifying protein and/or RNA, by obtaining a patient tissue sample (e.g., from biopsy tissue) and assaying it in vitro for RNA or protein levels, structure and/or activity of the expressed MDM2 protein-MDMIP complex (or the MDM2 protein and MDMIP mRNAs). Methods which are well-known within the art including, e.g., immunoassays to detect MDM2 protein-MDMIP complex (e.g., by Western blot analysis, immunoprecipitation followed by sodium dodecyl sulfate (SDS) polyacrylamide gel electrophoresis, immunocytochemistry, etc.) and/or hybridization assays to detect concurrent expression of the MDM2 protein and MDMIP mRNAs (e.g., Northern assays, dot blots, in situ hybridization, etc.). ps (ii) Disorders with Increased MDM2 Protein and MDM2 Protein-MDMIP Complex Levels The invention includes methods for the reduction of MDM2 protein-MDMIP complex expression (i.e., the expression of the two protein components of the complex and/or formation of the complex) by targeting mRNAs which express the protein moieties. RNA Therapeutics are differentiated into three classes: (i) antisense species; (ii) ribozymes or (iii) RNA aptamers. See e.g., Good, et al., 1997. Gene Therapy 4:45–54. Antisense therapy will be discussed below. Ribozyme therapy involves the administration (i.e., induced expression) of small RNA molecules with enzymatic ability to cleave, bind, or otherwise inactivate specific RNAs, thus reducing or eliminating the expression of particular proteins. See e.g., Grassi & Marini, 1996. Ann. Med. 28:499–510. RNA aptamers are specific RNA ligands for proteins, such as for Tat and Rev RNA (see e.g., Good, et al., 1997. Gene Therapy 4:45–54) which can specifically inhibit their translation.

In one embodiment, the activity or level of the MDM2 protein may be reduced by administration of MDMIP, a nucleic acid which encodes MDMIP or an antibody (or a derivative or fragment of the antibody possessing the binding domain thereof) which specifically binds to MDMIP. Similarly, the levels or activity of MDMIP may be reduced by administration of the MDM2 protein, a nucleic acid encoding the MDM2 protein or an antibody (or a derivative or fragment of the antibody possessing the binding domain thereof) which specifically binds the MDM2 protein. In another embodiment of the present invention, diseases or disorders which are associated with increased levels of the MDM2 protein or MDMIP, may be treated or prevented by administration of a Therapeutic which increases MDM2 protein-MDMIP complex formation, if the complex formation acts to reduce or inactivate the MDM2 protein or the particular MDMIP via MDM2 protein-MDMIP complex formation. Such diseases or disorders may be treated or prevented by: (i) the administration of one member of the MDM2 protein-MDMIP complex, including mutants of one or both of the proteins which possess increased affinity for the other member of the MDM2 protein-MDMIP complex (so as to cause increased complex formation) or ii) the administration of antibodies or other molecules which serve to stabilize the MDM2 protein-MDMIP complex, or the like.

Determination of the Biological Effect of the Therapeutic

In some embodiments, suitable in vitro or in vivo assays are utilized to determine the effect of a specific Therapeutic and whether its administration is indicated for treatment of the affected tissue.

For example, in vitro assays may be performed with representative cells of the type(s) involved in the patient's disorder, to determine if a given Therapeutic exerts the desired effect upon the cell type(s). Compounds for use in therapy may be tested in suitable animal model systems including, e.g. rats, mice, chicken, cows, monkeys, rabbits, and the like, prior to testing in human subjects. Similarly, for in vivo testing, any of the animal model system known in the art may be used prior to administration to human subjects. (i) Malignancies Components of the MDM2 protein-MDMIP complex are likely involved in the regulation of cell proliferation. Accordingly, Therapeutics of the present invention may be useful in the therapeutic or prophylactic treatment of diseases or disorders which are associated with cell hyperproliferation and/or loss of control of cell proliferation (e.g., cancers, malignancies and tumors). For a review of such hyperproliferation disorders, see e.g., Fishman, et al., 1985. Medicine, 2nd ed. (J.B. Lippincott Co., Philadelphia, Pa.).

Therapeutics of the present invention may be assayed by any method known within the art for efficacy in treating or preventing malignancies and related disorders. Such assays include, e.g., in vitro assays utilizing transformed cells or cells derived from the patient's tumor, as well as in vivo assays using animal models of cancer or malignancies. Potentially effective Therapeutics, for example, inhibit the proliferation of tumor-derived or transformed cells in culture or cause a regression of tumors in animal models, in comparison to the controls.

In the practice of the present invention, once a malignancy or cancer has been shown to be amenable to treatment by modulating (i.e., inhibiting, antagonizing or agonizing) MDM2 protein-MDMIP complex activity, that cancer or malignancy may subsequently be treated or prevented by the administration of a Therapeutic which serves to modulate MDM2 protein-MDMIP complex formation and function, including supplying MDM2 protein-MDMIP complex and the individual binding partners of the protein complex (i.e., the MDM2 protein and/or MDMIP).

(ii) Pre-Malignant Conditions

The Therapeutics of the present invention which are effective in the therapeutic or prophylactic treatment of cancer or malignancies may also be administered for the treatment of pre-malignant conditions and/or to prevent the progression of a pre-malignancy to a neoplastic or malignant state. Such prophylactic or therapeutic use is indicated in conditions known or suspected of preceding progression to neoplasia or cancer, in particular, where non-neoplastic cell growth consisting of hyperplasia, metaplasia or, most particularly, dysplasia has occurred. For a review of such abnormal cell growth see e.g., Robbins & Angell, 1976. *Basic Pathology*, 2nd ed (W.B. Saunders Co., Philadelphia, Pa.).

Hyperplasia is a form of controlled cell proliferation involving an increase in cell number in a tissue or organ, without significant alteration in its structure or function. For example, it has been demonstrated that endometrial hyperplasia often precedes endometrial cancer. Metaplasia is a form of controlled cell growth in which one type of mature or fully differentiated cell substitutes for another type of mature cell. Metaplasia may occur in epithelial or connective tissue cells. Dysplasia is generally considered a precursor of cancer, and is found mainly in the epithelia. Dysplasia is the most disorderly form of non-neoplastic cell growth, and involves a loss in individual cell uniformity and in the architectural orientation of cells. Dysplasia characteristically occurs where there exists chronic irritation or inflammation, and is often found in the cervix, respiratory passages, oral cavity, and gall bladder.

Alternatively, or in addition to the presence of abnormal cell growth characterized as hyperplasia, metaplasia, or dysplasia, the presence of one or more characteristics of a transformed or malignant phenotype displayed either in vivo or in vitro within a cell sample derived from a patient, is indicative of the desirability of prophylactic/therapeutic administration of a Therapeutic of the present invention which possesses the ability to modulate MDM2 protein•MDMIP complex activity. Characteristics of a transformed phenotype include, e.g.,: (i) morphological changes; (ii) looser substratum attachment; (iii) loss of cell-to-cell contact inhibition; (iv) loss of anchorage dependence; (v) protease release; (vi) increased sugar transport; (vii) decreased serum requirement; (viii) expression of fetal antigens, (ix) disappearance of the 250 Kdal cell-surface protein, and the like. See e.g., Richards, et al., 1986. *Molecular Pathology* (W.B. Saunders Co., Philadelphia, Pa.).

In one embodiment, a patient which exhibits one or more of the following predisposing factors for malignancy is treated by administration of an effective amount of a Therapeutic: (i) a chromosomal translocation associated with a malignancy (e.g., the Philadelphia chromosome (bcr/abl) for chronic myelogenous leukemia and t(14;18) for follicular lymphoma, etc.); (ii) familial polyposis or Gardner's syndrome (possible forerunners of colon cancer); (iii) monoclonal gammopathy of undetermined significance (a possible precursor of multiple myeloma) and (iv) a first degree kinship with persons having a cancer or pre-cancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia and Bloom's syndrome).

In another embodiment, a Therapeutic of the present invention is administered to a human patient to prevent the progression to breast, colon, lung, pancreatic, or uterine cancer, or melanoma or sarcoma.

(iii) Hyperproliferative and Dysproliferative Disorders

In a preferred embodiment of the present invention, a Therapeutic is administered in the therapeutic or prophylactic treatment of hyperproliferative or benign dysproliferative disorders. The efficacy in treating or preventing hyperproliferative diseases or disorders of a Therapeutic of the present invention may be assayed by any method known within the art. Such assays include in vitro cell proliferation assays, in vitro or in vivo assays using animal models of hyperproliferative diseases or disorders, or the like. Potentially effective Therapeutics may, for example, promote cell proliferation in culture or cause growth or cell proliferation in animal models in comparison to controls.

Once a hyperproliferative disorder has been shown to be amenable to treatment by modulation of MDM2 protein•MDMIP complex activity, the hyperproliferative disease or disorder may be treated or prevented by the administration of a Therapeutic which modulates MDM2 protein•MDMIP complex formation (including supplying MDM2 protein•MDMIP complex and the individual binding partners of a MDM2 protein•MDMIP complex.

In some embodiments, methods are directed to the treatment or prevention of cirrhosis of the liver (a condition in which scarring has overtaken normal liver regeneration processes); treatment of keloid (hypertrophic scar) formation causing disfiguring of the skin in which the scarring process interferes with normal renewal; psoriasis (a common skin condition characterized by excessive proliferation of the skin and delay in proper cell fate determination); benign tumors; fibrocystic conditions and tissue hypertrophy (e.g., benign prostatic hypertrophy).

Gene Therapy Using MDMIP and/or MDM2 Nucleic Acids

In one embodiment, nucleic acids comprising a sequence which encodes the MDM2 protein and/or MDMIP, or functional derivatives thereof, are administered to modulate MDM2 protein•MDMIP complex function, using gene therapy, i.e., a nucleic acid or nucleic acids encoding both the MDM2 protein and MDMIP, or functional derivatives thereof, are administered to a subject. After delivery of the nucleic acid to a subject, the nucleic acid expresses its encoded protein(s), which then serve to exert a therapeutic effect by modulating MDM2 protein•MDMIP complex function. Any of the methods relating to gene therapy available within the art may be used in the practice of the present invention. See, e.g., Goldspiel, et al.,. Clin. Pharm. 12:488–505, 1993, and U.S. Pat. No. 5,580,859.

In one embodiment, the Therapeutic includes a nucleic acid encoding an MDM2 protein and MDMIP nucleic acid which is part of an expression vector expressing both proteins, or fragments or chimeric proteins thereof, within a suitable host. In a specific embodiment, such a nucleic acid possesses a promoter which is operably-linked to the MDM2 protein and the MDMIP coding region(s), or, less preferably two separate promoters linked to the MDM2 protein and the MDMIP coding regions separately; wherein the promoter is inducible or constitutive, and, optionally, tissue-specific. In another specific embodiment, a nucleic acid molecule is used in which the MDM2 protein and MDMIP coding sequences (and any other desired sequences) are flanked by regions which promote homologous recombination at a desired site within the genome, thus providing for intra-chromosomal expression of the MDM2 protein and the MDMIP nucleic acids. See e.g., Koller & Smithies, 1989. Proc. Natl. Acad. Sci. USA 86:8932–8935.

Delivery of the Therapeutic nucleic acid into a patient may be either direct (i.e., the patient is directly exposed to the nucleic acid or nucleic acid-containing vector) or indirect (i.e., cells are first transformed with the nucleic acid in vitro, then transplanted into the patient). These two approaches are known, respectively, as in vivo or ex vivo gene therapy. For example, the nucleic acid can be directly administered in vivo, where it is expressed to produce the encoded product. This may be accomplished by any of numerous methods known in the art including, e.g.: (i) constructing it as part of an appropriate nucleic acid expression vector and administering in a manner such that it becomes intracellular (e.g., by infection using a defective or attenuated retroviral or other viral vector; see U.S. Pat. No. 4,980,286) or (ii) direct injection of naked DNA, or through the use of microparticle bombardment (e.g., a "Gene Gun"; Biolistic, Dupont), or by coating it with lipids, cell-surface receptors/transfecting agents, or through encapsulation in liposomes, microparticles, or microcapsules, or by administering it in linkage to a peptide which is known to enter the nucleus, or by administering it in linkage to a ligand predisposed to receptor-mediated endocytosis (see e.g., Wu & Wu, 1987. J. Biol. Chem. 262:4429–4432), which can be used to "target" cell types which specifically express the receptors of interest, etc.

In another specific embodiment of the present invention, a nucleic acid-ligand complex may be produced in which the ligand comprises a fusogenic viral peptide designed so as to disrupt endosomes, thus allowing the nucleic acid to avoid subsequent lysosomal degradation. In yet another specific embodiment, the nucleic acid may be targeted in vivo for cell-specific endocytosis and expression, by targeting a specific receptor. See e.g., PCT Publications WO 92/06180; WO93/14188 and WO 93/20221. Alternatively, the nucleic acid may be introduced intracellularly and incorporated within host cell genome for expression by homologous recombination. See e.g., Zijlstra, et al., 1989. Nature 342:435–438.

In yet another embodiment, a viral vector which contains the MDM2 protein and/or MDMIP nucleic acids is utilized. For example, retroviral vectors may be employed (see e.g., Miller, et al., 1993. Meth. Enzymol. 217:581–599) which have been modified to delete those retroviral-specific sequences which are not required for packaging of the viral genome and its subsequent integration into host cell DNA. The MDM2 protein and/or MDMIP (preferably both protein species) nucleic acids are cloned into the vector, which facilitates delivery of the genes into a patient. See e.g., Boesen, et al., 1994. Biotherapy 6:291–302; Kiem, et al., 1994. Blood 83:1467–1473. Additionally, adenovirus is an especially efficacious "vehicle" for the delivery of genes to the respiratory epithelia. Other targets for adenovirus-based delivery systems are liver, the central nervous system, endothelial cells, and muscle. Adenoviruses also possess the advantageous ability to infect non-dividing cells. For a review see e.g., Kozarsky & Wilson, 1993. Curr. Opin. Gen. Develop. 3:499–503. Adenovirus-associated virus has also been proposed for use in gene therapy. See e.g., Walsh, et al., 1993. Proc. Soc. Exp. Biol. Med. 204:289–300.

An additional approach to gene therapy in the practice of the present invention involves transferring a gene into cells in in vitro tissue culture by such methods as electroporation, lipofection, calcium phosphate-mediated transfection, or viral infection. Generally, the method of transfer includes the transfer of a selectable marker to the cells. The cells are then placed under selection pressure (e.g., antibiotic resistance) so as facilitate the isolation of those cells which have taken up, and are expressing the transferred gene. Those cells are then delivered to a patient. In this specific embodiment, the nucleic acid is introduced into a cell prior to the in vivo administration of the resulting recombinant cell by any method known within the art including, e.g.: transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methods which ensure that the necessary developmental and physiological functions of the recipient cells are not disrupted by the transfer. See e.g., Loeffler & Behr, 1993. Meth. Enzymol. 217: 599–618. The technique should provide for the stable transfer of the nucleic acid to the cell, so that the nucleic acid is expressible by the cell and preferably heritable and expressible by its cell progeny.

The resulting recombinant cells may be delivered to a patient by various methods known within the art including, e.g.: injection of epithelial cells (e.g., subcutaneously); the application of recombinant skin cells as a skin graft onto the patient and the intravenous injection of recombinant blood cells (e.g., hematopoetic stem or progenitor cells). The total amount of cells which are envisioned for use depend upon the desired effect, patient state, etc., and may be determined by one skilled within the art.

Cells into which a nucleic acid can be introduced for purposes of gene therapy encompass any desired, available cell type, and include e.g., epithelial cells, endothelial cells, keratinocytes, fibroblasts, muscle cells, hepatocytes and blood cells. In a preferred embodiment of the present invention, the cell utilized for gene therapy may be autologous to the patient.

In a specific embodiment in which recombinant cells are used in gene therapy, stem or progenitor cells, which can be isolated and maintained in vitro, may be utilized. Such stem cells include, e.g., hematopoietic stem cells (HSC), stem cells of epithelial tissues and neural stem cells (see e.g., Stemple & Anderson, 1992. Cell 71:973–985). Any technique which provides for the isolation, propagation, and maintenance in vitro of HSC may be used. HSCs utilized for gene therapy are, preferably, autologous to the patient. Hence, non-autologous HSCs are, preferably, utilized in conjunction with a method of suppressing transplantation immune reactions of the future host/patient. See e.g., Kodo, et al., 1984. J. Clin. Invest. 73:1377–1384. In another embodiment, HSCs may be highly enriched (or produced in a substantially-pure form), by any techniques known within the art, prior to administration to the patient. See e.g., Witlock & Witte, 1982. Proc. Natl. Acad. Sci. USA 79:3608-3612.

Anti-Sense MDMIP or MDM2 Oligonucleotides MDM2 protein-MDMIP complex formation and function may be inhibited by the use of anti-sense nucleic acids for the MDM2 protein and/or MDMIP. In some embodiments, nucleic acids (of at least six nucleotides in length) which are anti-sense to a genomic sequence (gene) or cDNA encoding the MDM2 protein and/or MDMIP, or portions thereof, are used prophylactically or therapeutically. Such anti-sense nucleic acids have utility as Therapeutics which inhibit MDM2 protein•MDMIP complex formation or activity, and may be utilized in a therapeutic or prophylactic manner.

The invention also provides methods for inhibiting expression of the MDM2 protein and MDMIP nucleic acid sequences within a prokaryotic or eukaryotic cell. The method includes providing the cell with an therapeutically-effective amount of an anti-sense nucleic acid of the MDM2 protein and MDMIP, or derivatives thereof.

The anti-sense nucleic acids may be oligonucleotides which may either be directly administered to a cell or which may be produced in vivo by transcription of the exogenous, introduced sequences. In addition, the anti-sense nucleic acid may be complementary to either a coding (i.e., exonic) and/or non-coding (i.e., intronic) region of the MDM2 protein or MDMIP mRNAs. The MDM2 protein and MDMIP anti-sense nucleic acids are, at least, six nucleotides in length and are, preferably, oligonucleotides ranging from 6–200 nucleotides in length. In specific embodiments, the anti-sense oligonucleotide is at least 10 nucleotides, at least 15 nucleotides, at least 100 nucleotides, or at least 200 nucleotides. The anti-sense oligonucleotides may be DNA or RNA (or chimeric mixtures, derivatives or modified versions thereof), may be either single-stranded or double-stranded and may be modified at a base, sugar or phosphate backbone moiety.

In addition, the anti-sense oligonucleotide may include other associated functional groups, such as peptides, moieties which facilitate the transport of the oligonucleotide across the cell membrane, a hybridization-triggered cross-linking agent, a hybridization-triggered cleavage-agent, and the like. See e.g., Letsinger, et al., 1989. *Proc. Natl. Acad. Sci. U.S.A.* 86:6553–6556; PCT Publication No. WO 88/09810. In a specific embodiment, the MDM2 protein and MDMIP antisense oligonucleotides include catalytic RNAs or ribozymes. See, e.g., Sarver, et al., 1990. *Science* 247:1222–1225.

The anti-sense oligonucleotides may be synthesized by standard methods known within the art including, e.g.: (i) automated phosphorothioate-mediated oligonucleotide synthesis (see e.g., Stein, et al., 1988. *Nuc. Acids Res.* 16:3209) or (ii) methylphosphonate oligonucleotides can be prepared by use of controlled pore glass polymer supports (see e.g., Sarin, et al., 1988. *Proc. Natl. Acad. Sci. U.S.A*. 85:7448–7451).

In an alternative embodiment, the MDM2 protein and MDMIP antisense nucleic acids are produced intracellularly by transcription of an exogenous sequence. For example, a vector may be produced and (upon being exocytosed by the cell) transcribed in vivo, thus producing an antisense nucleic acid (RNA) species. The vector may either remain episomal or become chromosomally-integrated, so long as it can be transcribed to produce the desired antisense RNA. The vectors may be derived from bacterial, viral, yeast or other sources known within the art, which are utilized for replication and expression in mammalian cells. Expression of the sequences encoding the MDM2 protein and MDMIP antisense RNAs may be facilitated by any promoter known within the art to function in mammalian, preferably, human cells. Such promoters may be inducible or constitutive and include, e.g.,: (i) the SV40 early promoter region; (ii) the promoter contained in the 3'-terminus long terminal repeat of Rous sarcoma virus (RSV); (iii) the Herpesvirus thymidine kinase promoter and (iv) the regulatory sequences of the metallothionein gene.

The MDM2 protein and MDMIP antisense nucleic acids may be utilized prophylactically or therapeutically in the treatment or prevention of disorders of a cell type which expresses (or over-expresses) the MDM2 protein-MDMIP complex. Cell types which express or over-express the MDM2 protein and MDMIP RNA may be identified by various methods known within the art including, e.g., hybridization with MDM2 protein- and MDMIP-specific nucleic acids (e.g., by Northern hybridization, dot blot hybridization, in situ hybridization) or by observing the ability of RNA from the specific cell type to be translated in vitro into the MDM2 protein and the MDMIP by immuno-histochemistry. If desired, primary tissue from a patient may be assayed for the MDM2 protein and/or MDMIP expression prior to actual treatment by, for example, immunocytochemistry or in situ hybridization.

Pharmaceutical compositions which include an effective amount of a MDM2 protein and MDMIP antisense nucleic acid contained within a pharmaceutically-acceptable carrier may be administered to a patient having a disease or disorder which is of a type that expresses or over-expresses MDM2 protein-MDMIP complex RNA or protein. The amount of MDM2 protein and/or MDMIP antisense nucleic acid which will be effective in the treatment of a particular disorder or condition will be dependant upon the nature of the disorder or condition, and may be determined by standard clinical techniques. Where possible, it is desirable to determine the antisense cytotoxicity in vitro, and then in useful animal model systems prior to testing and use in humans. In a specific embodiment, pharmaceutical compositions comprising MDM2 protein and MDMIP antisense nucleic acids may be administered via liposomes, microparticles, or microcapsules. See e.g., Leonetti, et al., 1990. *Proc. Natl. Acad. Sci. U.S.A.* 87:2448–2451.

MDM2 Protein-MDMIP Complex Assays

The functional activity of MDM2 protein-MDMIP complexes (and derivatives, fragments, analogs and homologs thereof) may be assayed by a number of methods known within the art. For example, putative modulators (e.g., inhibitors, agonists and antagonists) of MDM2 protein-MDM2 protein complex activity (e.g., anti-MDM2 protein-MDMIP complex antibodies, as well as MDM2 protein or MDMIP antisense nucleic acids) may be assayed for their ability to modulate MDM2 protein-MDMIP complex formation and/or activity.

(i) Immunoassays

Also disclosed herein are immunoassay-based useful for measuring the ability of an altered complex, e.g. a complex containing derivatives, fragments, analogs and/or homologs thereof of an MDM2 or MDMIP polypeptide to bind to, or compete with, wild-type MDM2 protein•MDMIP complex or MDMIP. Alternatively, immunoassays be used to determine the ability of the altered complex to bind to an anti-MDM2 protein-MDMIP complex antibody. These immunoassays include, e.g., competitive and non-competitive assay systems utilizing techniques such as radioimmunoassays, enzyme linked immunosorbent assay (ELISA), "sandwich" immunoassays, immunoradiometric assays, gel diffusion precipitin reactions, immunodiffusion assays, in situ immunoassays (e.g., using colloidal gold, enzyme or radioisotope labels), Western blots, Northwestern blots, precipitation reactions, agglutination assays (e.g., gel agglutination assays, hemagglutination assays), complement fixation assays, immunofluorescence assays, protein-A assays and immunoelectrophoresis assays, and the like. In one specific embodiment of the present invention, antibody binding is detected by assaying for a label on the primary antibody. In another specific embodiment, the binding of the primary antibody is ascertained by the detection of the binding of a secondary antibody (or reagent) specific for the primary antibody. In a further embodiment, the secondary antibody is labeled.

(ii) Gene Expression Assays

The expression of the MDM2 protein or MDMIP genes (both endogenous genes and those expressed from recombinant DNA) may be detected using techniques known within the art including, e.g.: Southern hybridization, Northern hybridization, restriction endonuclease mapping, DNA sequence analysis and polymerase chain reaction amplification (PCR) followed by Southern hybridization or RNase protection (see e.g, *Current Protocols in Molecular Biology* 1997. (John Wiley and Sons, New York, N.Y.)) with probes specific for the MDM2 protein and MDMIP genes in various cell types.

In one specific embodiment of the present invention, Southern hybridization may be used to detect genetic linkage of the MDM2 protein and/or MDMIP gene mutations to physiological or pathological states. Numerous cell types, at various stages of development, may be characterized for their expression of the MDM2 protein and MDMIP (particularly the concomitant expression of the MDM2 protein and MDMIP within the same cells). The stringency of the hybridization conditions for Northern or Southern blot analysis may be manipulated to ensure detection of nucleic acids with the desired degree of relatedness to the specific probes used. Modification of these aforementioned methods, as well as other methods well-known within the art, may be utilized in the practice of the present invention.

(iii) Binding Assays

Derivatives, fragments, analogs and homologs of MDMIP may be assayed for binding to the MDM2 protein by any method known within the art including, e.g.: (i) the modified yeast two hybrid assay system; (ii) immunoprecipitation with an antibody which binds to the MDM2 protein within a complex, followed by analysis by size fractionation of the immunoprecipitated proteins (e.g., by denaturing or non-denaturing polyacrylamide gel electrophoresis); (iii) Western analysis; (v) non-denaturing gel electrophoresis, and the like.

(iv) Assays for Biological Activity

A specific embodiment of the present invention provides a method for the screening of a derivative, fragment, analog or homolog of the MDM2 protein for biological activity. The method includes contacting a derivative, fragment, analog or homolog of the MDM2 protein with MDMIP and detecting the formation of a complex between the derivative, fragment, analog or homolog of the MDM2 protein and MDMIP. Detection of the formation of the complex indicates that the MDM2 protein derivative, fragment, analog or homolog, possesses biological (e.g., binding) activity. Similarly, an additional embodiment discloses a method for the screening a derivative, fragment, analog or homolog of MDMIP for biological activity. In this method, the derivative, fragment, analog or homolog of the protein is contacted with the MDM2 protein. And formation of a complex between the derivative, fragment, analog or homolog of MDMIP and the MDM2 protein is detected. Detecting he formation of the complex indicates that the MDMIP derivative, fragment, analog, or homolog possesses biological activity.

(10) Modulation of MDM2 Polypeptide Activity (i) Tumorigenesis

The MDM2 protein is reported to play a role in the control of cell proliferation as well as cell-transformation and tumorigenesis. The present invention discloses methods for screening MDM2 protein•MDMIP complexes (and derivatives, fragments, analogs and homologs, thereof) for its ability to alter cell proliferation, cell transformation and/or tumorigenesis in vitro and in vivo.

The MDM2 protein•MDMIP complex (and derivatives, fragments, analogs and homologs, thereof) may also be screened for activity in inducing or inhibiting cell transformation (or the progression to malignant phenotype) in vitro. The proteins and protein complex of the present invention may be screened by contacting either cells with a normal phenotype (for assaying for cell transformation) or a transformed cell phenotype (for assaying for inhibition of cell transformation) with the protein or protein complex of the present invention and examining the cells for acquisition or loss of characteristics associated with a transformed phenotype (a set of in vitro characteristics associated with a tumorigenic ability in vivo) including, e.g.: colony formation in soft agar, a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250 Kdal cell-surface protein, and the like. See e.g., Luria, et al., 1978. *General Virology*, 3rd ed (John Wiley & Sons, New York, N.Y.).

The MDM2 protein•MDMIP complex (and derivatives, fragments, analogs and homologs, thereof) may also be screened for activity to promote or inhibit tumor formation in vivo in non-human test animal. A vast number of animal models of hyperproliferative disorders (e.g., tumorigenesis and metastatic spread) are known within the art. See e.g., Lovejoy, et al., 1997. *J Pathol.* 181:130–135. In a specific embodiment of the present invention, the proteins and protein complex may be administered to a non-human test animal (preferably a test animal predisposed to develop a type of tumor) and the non-human test animals is subsequently examined for an increased incidence of tumor formation in comparison with controls animals which were not administered the proteins or protein complex of the present invention. Alternatively, the proteins and protein complex may be administered to non-human test animals possessing tumors (e.g., animals in which tumors have been induced by introduction of malignant, neoplastic, or transformed cells or by administration of a carcinogen) and subsequently examining the tumors within the test animals for tumor regression in comparison to controls. Accordingly, once a hyperproliferative disease or disorder has been shown to be amenable to treatment by modulation of MDM2 protein•MDMIP complex activity that disease or disorder may be treated or prevented by administration of a Therapeutic which modulates MDM2 protein•MDMIP complex formation.

MDM2-MDMIP Interaction Assays

The present invention discloses methods for assaying and screening derivatives, fragments, analogs and homologs of MDMIP for binding to MDM2 protein. The derivatives, fragments, analogs and homologs of the MDMIP which interact with MDM2 protein may be identified by means of a yeast two hybrid assay system (see e.g., Fields & Song, 1989. *Nature* 340:245–246) or; preferably, a modification and improvement thereof, as described in U.S. patent applications Ser. Nos. 08/663,824 (filed Jun. 14, 1996) and 08/874,825 (filed Jun. 13, 1997), both of which are entitled "Identification and Comparison of Protein-Protein Interactions that Occur in Populations and Identification of Inhibitors of These Interactions," to Nandabalan, et al., and which are incorporated by reference herein in their entireties.

The identification of interacting proteins by the improved yeast two hybrid system is based upon the detection of the expression of a reporter gene (hereinafter "Reporter Gene"), the transcription of which is dependent upon the reconstitution of a transcriptional regulator by the interaction of two proteins, each fused to one half of the transcriptional regulator. The bait MDM2 protein (or derivative, fragment, analog or homolog) and prey protein (proteins to be tested for ability to interact with the bait protein) are expressed as fusion proteins to a DNA-binding domain, and to a transcriptional regulatory domain, respectively, or vice versa. In a specific embodiment of the present invention, the prey population may be one or more nucleic acids encoding mutants of MDMIP (e.g., as generated by site-directed mutagenesis or another method of producing mutations in a nucleotide sequence). Preferably, the prey populations are proteins encoded by DNA (e.g., cDNA, genomic DNA or synthetically generated DNA). For example, the populations may be expressed from chimeric genes comprising cDNA sequences derived from a non-characterized sample of a population of CDNA from mammalian RNA. In another specific embodiment, recombinant biological libraries expressing random peptides may be used as the source of prey nucleic acids.

The present invention discloses methods for the screening for inhibitors of MDMIP. In brief, the protein-protein interaction assay may be performed as previously described herein, with the exception that it is performed in the presence of one or more candidate molecules. A resulting increase or decrease in Reporter Gene activity, in relation to that which was present when the one or more candidate molecules are absent, indicates that the candidate molecule exerts an effect on the interacting pair. In a preferred embodiment, inhibition of the protein interaction is necessary for the yeast cells to survive, for example, where a non-attenuated protein interaction causes the activation of the URA3 gene, causing yeast to die in medium containing the chemical 5-fluoroorotic acid. See e.g., Rothstein, 1983. *Meth. Enzymol.* 101:167–180.

In general, the proteins comprising the bait and prey populations are provided as fusion (chimeric) proteins, preferably by recombinant expression of a chimeric coding sequence containing each protein contiguous to a pre-selected sequence. For one population, the pre-selected sequence is a DNA-binding domain that may be any DNA-binding domain, so long as it specifically recognizes a DNA sequence within a promoter (e.g., a transcriptional activator or inhibitor). For the other population, the pre-selected sequence is an activator or inhibitor domain of a transcriptional activator or inhibitor, respectively. The regulatory domain alone (not as a fusion to a protein sequence) and the DNA-binding domain alone (not as a fusion to a protein sequence) preferably, do not detectably interact, so as to avoid false-positives in the assay. The assay system further includes a reporter gene operably linked to a promoter that contains a binding site for the DNA-binding domain of the transcriptional activator (or inhibitor). Accordingly, binding of the MDM2 protein fusion protein to a prey fusion protein leads to reconstitution of a transcriptional activator (or inhibitor), which concomitantly activates (or inhibits) expression of the Reporter Gene.

In a specific embodiment, the present invention discloses a method for detecting one or more protein-protein interactions comprising the following steps: (i) recombinantly-expressing the MDM2 protein (or a derivative, fragment, analog or homolog thereof) in a first population of yeast cells of a first mating type and possessing a first fusion protein containing the MDM2 protein sequence and a DNA-binding domain; wherein the first population of yeast cells contains a first nucleotide sequence operably-linked to a promoter which is "driven" by one or more DNA-binding sites recognized by the DNA-binding domain such that an interaction of the first fusion protein with a second fusion protein (comprising a transcriptional activation domain) results in increased transcription of the first nucleotide sequence; (ii) negatively selecting to eliminate those yeast cells in the first population in which the increased transcription of the first nucleotide sequence occurs in the absence of the second fusion protein; (iii) recombinantly expressing in a second population of yeast cells of a second mating type different from the first mating type, a plurality of the second fusion proteins; wherein the second fusion protein is comprised of a sequence of a derivative, fragment, analog or homolog of a MDMIP and an activation domain of a transcriptional activator, in which the activation domain is the same in each the second fusion protein; (iv) mating the first population of yeast cells with the second population of yeast cells to form a third population of diploid yeast cells, wherein the third population of diploid yeast cells contains a second nucleotide sequence operably linked to a promoter "driven" by a DNA-binding site recognized by the DNA-binding domain such that an interaction of a first fusion protein with a second fusion protein results in increased transcription of the second nucleotide sequence, in which the first and second nucleotide sequences can be the same or different and (v) detecting the increased transcription of the first and/or second nucleotide sequence, thereby detecting an interaction between a first fusion protein and a second fusion protein.

In a preferred embodiment, the bait (a MDM2 protein sequence) and the prey (a library of chimeric genes) are combined by mating the two yeast strains on solid media for a period of approximately 6–8 hours. In a less preferred embodiment, the mating is performed in liquid media. The resulting diploids contain both types of chimeric genes (i.e., the DNA-binding domain fusion and the activation domain fusion). After an interactive population is obtained, the DNA sequences encoding the pairs of interactive proteins are isolated by a method wherein either the DNA-binding domain hybrids or the activation domain hybrids are amplified, in separate reactions. Preferably, the amplification is carried out by polymerase chain reaction (PCR; see e.g., Innis, et al., 1990. PCR Protocols (Academic Press, Inc., San Diego, Calif.)) utilizing pairs of oligonucleotide primers specific for either the DNA-binding domain hybrids or the activation domain hybrids. The PCR amplification reaction may also be performed on pooled cells expressing interacting protein pairs, preferably pooled arrays of interactants. Other amplification methods known within the art may also be used including, e.g., ligase chain reaction; Qβ-replicase or the like. See e.g., Kricka, et al., 1995. *Molecular Probing, Blotting, and Sequencing* (Academic Press, New York, N.Y.).

In an additional embodiment of the present invention, the plasmids encoding the DNA-binding domain hybrid and the activation domain hybrid proteins may also be isolated and cloned by any of the methods well-known within the art. For example, but not by way of limitation, if a shuttle (yeast to *E. coli*) vector is used to express the fusion proteins, the genes may be subsequently recovered by transforming the yeast DNA into *E. coli* and recovering the plasmids from the bacteria. See e.g., Hoffman, et al., 1987. *Gene* 57:267–272.

Pharmaceutical Compositions

The invention present discloses methods of treatment and prophylaxis by the administration to a subject of an pharmaceutically-effective amount of a Therapeutic of the invention. In a preferred embodiment, the Therapeutic is substantially purified and the subject is a mammal, and most preferably, human.

Formulations and methods of administration that can be employed when the Therapeutic comprises a nucleic acid as described above. Various delivery systems are known and can be used to administer a Therapeutic of the present invention including, e.g.: (i) encapsulation in liposomes, microparticles, microcapsules; (ii) recombinant cells capable of expressing the Therapeutic; (iii) receptor-mediated endocytosis (see, e.g., Wu & Wu, 1987. *J. Biol. Chem.* 262:4429–4432); (iv) construction of a Therapeutic nucleic acid as part of a retroviral or other vector, and the like.

Methods of administration include, e.g., intradermal, intramuscular, intraperitoneal, intravenous, subcutaneous, intranasal, epidural, and oral routes. The Therapeutics of the present invention may be administered by any convenient route, for example by infusion or bolus injection, by absorption through epithelial or mucocutaneous linings (e.g., oral mucosa, rectal and intestinal mucosa, etc.) and may be administered together with other biologically-active agents. Administration can be systemic or local. In addition, it may be advantageous to administer the Therapeutic into the central nervous system by any suitable route, including intraventricular and intrathecal injection. Intraventricular injection may be facilitated by an intraventricular catheter attached to a reservoir (e.g., an Ommaya reservoir). Pulmonary administration may also be employed by use of an inhaler or nebulizer, and formulation with an aerosolizing agent. It may also be desirable to administer the Therapeutic locally to the area in need of treatment; this may be achieved by, for example, and not by way of limitation, local infusion during surgery, topical application, by injection, by means of a catheter, by means of a suppository, or by means of an implant. In a specific embodiment, administration may be by direct injection at the site (or former site) of a malignant tumor or neoplastic or pre-neoplastic tissue.

In another embodiment of the present invention, the Therapeutic may be delivered in a vesicle, in particular a liposome. See e.g., Langer, 1990. *Science* 249:1527–1533. In yet another embodiment, the Therapeutic can be delivered in a controlled release system including, e.g.: a delivery pump (see e.g., Saudek, et al., 1989. *New Engl. J. Med.* 321:574 and a semi-permeable polymeric material (see e.g., Howard, et al., 1989. *J. Neurosurg.* 71:105). Additionally, the controlled release system can be placed in proximity of the therapeutic target (e.g., the brain), thus requiring only a fraction of the systemic dose. See, e.g., Goodson, In: *Medical Applications of Controlled Release* 1984. (CRC Press, Bocca Raton, Fla.).

In a specific embodiment of the present invention, where the Therapeutic is a nucleic acid encoding a protein, the Therapeutic nucleic acid may be administered in vivo to promote expression of its encoded protein, by constructing it as part of an appropriate nucleic acid expression vector and administering it so that it becomes intracellular (e.g., by use of a retroviral vector, by direct injection, by use of microparticle bombardment, by coating with lipids or cell-surface receptors or transfecting agents, or by administering it in linkage to a homeobox-like peptide which is known to enter the nucleus (see e.g., Joliot, et al., 1991. *Proc. Natl. Acad Sci. USA* 88:1864–1868), and the like. Alternatively, a nucleic acid Therapeutic can be introduced intracellularly and incorporated within host cell DNA for expression, by homologous recombination.

The present invention also provides pharmaceutical compositions. Such compositions comprise a therapeutically-effective amount of a Therapeutic, and a pharmaceutically acceptable carrier. As utilized herein, the term "pharmaceutically acceptable" means approved by a regulatory agency of the Federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

The amount of the Therapeutic of the invention which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. However, suitable dosage ranges for intravenous administration of the Therapeutics of the present invention are generally about 20–500 micrograms (ag) of active compound per kilogram (Kg) body weight. Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient.

The present invention also provides a pharmaceutical pack or kit, comprising one or more containers filled with one or more of the ingredients of the pharmaceutical compositions and Therapeutics of the present invention. Optionally associated with such container(s) may be a notice in the form prescribed by a governmental agency regulating the manufacture, use or sale of pharmaceuticals or biological products, which notice reflects approval by the agency of manufacture, use or sale for human administration.

The invention will be further described in the following examples, which do not limit the scope of the invention described in the claims.

EXAMPLE 1

Identification of a Complex Including an MDM2-Derived Polypeptide and a Novel MDM2-Interacting Polypeptide To identify proteins which bind to MDM2 proteins, expression vectors which encode proteins for use in a yeast two hybrid bait-prey screening assay were constructed. A cDNA encoding an MDM2-derived polypeptide was used to produce the bait polypeptide and libraries of human cDNA were used to produce prey polypeptides. The MDM2 bait polypeptide was encoded by the human MDM2 nucleotide sequence nucleotides 312–963 in the nucleic acid sequence having GenBank Accession Number M92424; Oliner et al., Nature 358:80–83, 1992. The encoded MDM2 bait polypeptide was fused to the GAL4 activator domain.

The prey cDNAs were obtained from a human fetal brain cDNA library of $1.5 \times 10^6$ independent isolates. The library was synthesized from Xho 1-digested and T15-primed fetal brain mRNA (derived from five male/female, 19–22 week fetuses). The prey cDNAs were directionally cloned into pBD-GAL4 (Stratagene; La Jolla, Calif.). This plasmid is a yeast Gal4 activation domain cloning vector and which also includes the TRP1 gene for selection of yeast deficient in tryptophan biosynthesis.

The plasmid construct encoding the MDM2 bait polypeptide was transformed by lithium acetate-polyethylene glycol-mediated transformation (see e.g., Ito, et al., J. Bacteriol. 153:163–168, 1983) into the yeast strain N106r (mating type a, ura3, his3, ade2, trp1, leu2, gal4, gal80, cyh$^r$, Lys2::GAL1$_{UAS}$-HIS3$_{TATA}$-HIS3, ura3::GAL1$_{UAS}$-GAL$_{TATA}$-lacZ). Plasmids containing prey sequences were transformed into yeast strain YULH (mating type á, ura3, his3, lys2, Ade2, trp1, leu2, gal4, gal80, GAL1-URA3, GAL1-lacZ). The transformed yeast populations were then mated using standard methods in the art. See e.g., Sherman, et al., *Getting Started with Yeast* (Academic Press; New York, N.Y.), 1991. In brief, the yeast cells were grown until mid- to late-log phase on media that selected for the presence of the appropriate plasmids. The two mating strains (α and a) were then diluted in YAPD media, filtered onto nitrocellulose membranes and incubated at 30° C. for 6–8 hours. The yeast cells were then transferred to media selective for the desired diploids (i.e., yeast harboring reporter genes for β-galactosidase, uracil auxotrophy, and histidine auxotrophy and expression of the vectors encoding the bait and prey). The mating products were then plated onto synthetic complete (SC) media (see e.g., Kaiser, et al., *Methods in Yeast Genetics* (Cold Spring Harbor Laboratory Press; Cold Spring Harbor, N.Y.) 1994.) lacking adenine and lysine (to facilitate the selection of successful matings), leucine and tryptophan (to facilitate the selection for expression of genes encoded by both the bait and prey plasmids) and uracil and histidine (to facilitate the selection for protein interactions). This medium is referred to as SC Selective medium (hereinafter "SCS medium").

Isolates selected for successful mating, expressing both fusion constructs, and expressing interacting proteins were selected for further analysis.

Selected clones were first examined for expression of β-galactosidase to confirm the formation of an interaction between the bait MDM2 protein fragment and a prey polypeptide. Filter-lift β-galactosidase assays were performed using a protocol modified from Breeden et al., Cold Spring Harbor Quant. Biol. 50:643–650, 1985. Colonies were patched onto SCS plates, grown overnight and replica-plated onto Whatman No. 1 filters. The replica filters were subsequently assayed for β-galactosidase activity. Colonies which were positive turned blue in color.

Cells from positive colonies were individually plated and regrown as single isolates in the individual wells of 96-well microtiter plates. Ten microliters (µl) of each isolate was lysed, the inserts contained within the pACT2 and pBD-GAL4 plasmids were amplified by PCR using primers specific for the flanking sequences of each vector. Approximately 200 amino-terminal nucleotides of each insert sequence was determined using an ABI Model 377 sequenator. Comparison to known sequences was made using the "BLAST" computer program publicly available through the National Center for Biotechnology Information.

Six different isolates were identified. Four of those were determined to encode polypeptides sequences identical to already known proteins which interact with MDM2. These polypeptides include human p53 cellular tumor antigen (GenBank Acc. No. X54156), retinoblastoma protein (pRB; GenBank Acc. No. M28419), E2F-1 (a pRB-binding protein with properties of transcription factor E2F) nucleic acid sequence (GenBank Acc. No. M96577), and ubiquitin (GenBank Acc. No. U49869).

One isolate encoding an MDM2-interacting polypeptide include a nucleic acid sequence that has not been previously described. The nucleic acid sequence and its encoded polypeptide was named MDMIP, for MDM-Interacting Polypeptide. The nucleic acid sequence and the amino acid sequence of the encoded polypeptide are shown in FIG. 1 and SEQ ID NO:1 and SEQ ID NO:2, respectively.

EXAMPLE 2

Determining the Specificity of MDM2 Protein-MDIP Interactions

To determine the overall degree of specificity for the MDM2-MDMIP interactions, two general assays were performed. In the first assay, N106r yeast cells were produced which expressed the individual plasmids encoding the MDM2 proteins. These yeast cells were plated on SCS plates, grown overnight, and examined for growth. No growth was found for the novel interactant. This result confirms that MDM2 is not a "self-activating" protein. Instead, MDM2 protein requires interaction with a second protein domain for a functional activation complex.

In the second assay, a plasmid containing the MDMIP insert was transformed into strain YULH yeast (mating type a) and mated with yeast strain N106r (mating type a) expressing proteins other than the MDM2 protein. Promiscuous binders (i.e., inserts able to bind with many other proteins in a non-specific manner) interact in a non-specific manner with non-MDM2 protein domains, and are subsequently discarded as non-specific interactants. MDMIP did not show binding to proteins other than MDM2.

To further demonstrate the reproducibility and specificity of the MDM2-MDMIP interactions, the isolated bait plasmid for the MDM2 protein was used to transform yeast N106r (mating type α). The interacting domain from MDMIP was transformed into strain YULH (mating type a). The transformants were re-amplified, and a mating was performed to recapitulate the identified MDM2 protein•MDMIP interaction. The MDM2 protein was shown to complex in a specific manner with MDMIP. In addition, the MDM2 protein did not show any non-specifically reaction with the CDK2 protein or vector controls.

EXAMPLE 3

Analysis of MDMIP Nucleic Acid and its Encoded Polypeptide Sequence

The MDMIP nucleic acid sequence was examined for homology to other nucleic acids and for the presence of open reading frames.

The MDMIP nucleic acid sequence of 486 nucleotides (SEQ ID NO:1) was found to be 88% identical to soares melanocyte EST N28611, a human cDNA clone of 440 nucleotides. However, since the identities were found only between nucleotides 87 and 371 of MDMIP and nucleotides 83 and 372 of EST N28611, MDMIP could not be extended in either direction with EST N28611. Further searches did not reveal homologies to other ESTs. Thus, the assembled sequence could not be extended in either the 5' or 3' direction.

The MDMIP nucleotide sequence is also approximately 60% homologous at nucleotides 86 to 418 to the cDNA sequence of the human glutamate pyruvate transaminase (GenBank Accession Number U70732; Sohocki et al., Genomics 40: 247–252, 1997).

An open reading frame (ORF) is present in the MDMIP nucleic acid from nucleotides 1-222. A BlastP search with the MDMIP amino acid sequence showed no homology to previously describe sequences. The translated reading frame contains no initiator methionine codon (ATG), but has a stop codon at amino acid position 75. The protein therefor most likely represents the carboxy terminal region of a protein. The amino acid in position 5 (NAA) could be Glu (GAA), Gln (CAA), Lys (AAA), or a stop codon (TAA); the amino acid in position 58 (TNT) could be Phe (TTT), Ser (TCT), Tyr (TAT), or Cys (TGT).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid encoding an MDMIP polypeptide, wherein the nucleic acid comprises the nucleic acid sequence of SEQ ID NO:1.

2. A vector comprising the nucleic acid of claim 1.

3. A cell comprising the vector of claim 2.

4. A composition comprising the nucleic acid of claim 1.

* * * * *

SEQUENCE LISTING

<160> NUMBER OF SEQ ID NOS: 4

<210> SEQ ID NO 1
<211> LENGTH: 486
<212> TYPE: DNA
<213> ORGANISM: Homo sapiens
<220> FEATURE:
<223> OTHER INFORMATION: Any N is A, C, G, or T

<400> SEQUENCE: 1

| | | | | | |
|---|---|---|---|---|---|
| gcacgagcgt | atnaaaaaat | gttttccatg | tttatggaaa | aggctgggaa | gtgctggtgt | 60 |
| aaaatgccca | agctcataat | agatactcct | ttctccattg | ttgcccctgc | tctaactgct | 120 |
| gttctttctt | gccagcttcg | ttgttccctc | tggcttgtgg | gggcacggct | gtntccatgt | 180 |
| ggcaaggtgg | aaggcatgga | cgtgtggagg | aggcgctgga | gctgaaggaa | tggacgagcc | 240 |
| ctgggaggag | ggcagaaggc | tacgcagggc | tgaggatgaa | gatgcagccc | ctggatngtc | 300 |
| cccagactct | caggacattg | cccagtcaag | ggttcgagcc | acnaggnctt | ggctcatatg | 360 |
| gcatgaaggg | gaacttgcat | aagaagcccc | ctccctggtt | gtggtcctgg | ccctctgttc | 420 |
| tggaaaactg | gntcntagnc | ccctggtttt | ttngcaaagc | ctgaagaaag | ggaaantccc | 480 |
| catggg | | | | | | 486 |

<210> SEQ ID NO 2
<211> LENGTH: 74
<212> TYPE: PRT
<213> ORGANISM: Homo sapiens
<220> FEATURE:
<223> OTHER INFORMATION: Any X can be any amino acid.

<400> SEQUENCE: 2

Ala Arg Ala Tyr Xaa Lys Met Phe Ser Met Phe Met Glu Lys Ala Gly
 1               5                  10                  15

Lys Cys Trp Cys Lys Met Pro Lys Leu Ile Ile Asp Thr Pro Phe Ser
            20                  25                  30

Ile Val Ala Pro Ala Leu Thr Ala Val Leu Ser Cys Gln Leu Arg Cys
        35                  40                  45

Ser Leu Trp Leu Val Gly Ala Arg Leu Xaa Pro Cys Gly Lys Val Glu
    50                  55                  60

Gly Met Asp Val Trp Arg Arg Arg Trp Ser

<210> SEQ ID NO 3
<211> LENGTH: 652
<212> TYPE: DNA
<213> ORGANISM: Homo sapiens

<400> SEQUENCE: 3

```
atgtgcaata ccaacatgtc tgtacctact gatggtgctg taaccacctc acagattcca      60
gcttcggaac aagagaccct ggttagacca aagccattgc ttttgaagtt attaaagtct     120
gttggtgcac aaaaagacac ttatactatg aaagaggttc ttttttatct tggccagtat     180
attatgacta aacgattata tgatgagaag caacaacata ttgtatattg ttcaaatgat     240
cttctaggag atttgtttgg cgtgccaagc ttctctgtga agagcacag gaaaatatat       300
accatgatct acaggaactt ggtagtagtc aatcagcagg aatcatcgga ctcaggtaca     360
tctgtgagtg agaacaggtg tcaccttgaa ggtgggagtg atcaaaagga ccttgtacaa     420
gagcttcagg aagagaaacc ttcatcttca catttggttt ctagaccatc tacctcatct     480
agaaggagag caattagtga gacagaagaa aattcagatg aattatctgg tgaacgacaa     540
agaaaacgcc acaaatctga tagtatttcc ctttcctttg atgaaagcct ggctctgtgt     600
gtaataaggg agatatgttg tgaaagaagc agtagcagtg aatctacagg ga              652
```

<210> SEQ ID NO 4
<211> LENGTH: 216
<212> TYPE: PRT
<213> ORGANISM: Homo sapiens

<400> SEQUENCE: 4

```
Met Cys Asn Thr Asn Met Ser Val Pro Thr Asp Gly Ala Val Thr Thr
  1               5                  10                  15

Ser Gln Ile Pro Ala Ser Glu Gln Glu Thr Leu Val Arg Pro Lys Pro
             20                  25                  30

Leu Leu Leu Lys Leu Leu Lys Ser Val Gly Ala Gln Lys Asp Thr Tyr
         35                  40                  45

Thr Met Lys Glu Val Leu Phe Tyr Leu Gln Tyr Ile Met Thr Lys Arg
     50                  55                  60

Leu Tyr Asp Glu Lys Gln Gln His Ile Val Tyr Cys Ser Asn Asp Leu
 65                  70                  75                  80

Leu Gly Asp Leu Phe Gly Val Pro Ser Phe Ser Val Lys Glu His Arg
                 85                  90                  95

Lys Ile Tyr Thr Met Ile Tyr Arg Asn Leu Val Val Val Asn Gln Gln
            100                 105                 110

Glu Ser Ser Asp Ser Gly Thr Ser Val Ser Glu Asn Arg Cys His Leu
        115                 120                 125

Glu Gly Gly Ser Asp Gln Lys Asp Leu Val Gln Glu Leu Gln Glu Glu
    130                 135                 140

Lys Pro Ser Ser Ser His Leu Val Ser Arg Pro Ser Thr Ser Ser Arg
145                 150                 155                 160

Arg Arg Ala Ile Ser Glu Thr Glu Glu Asn Ser Asp Glu Leu Ser Gly
                165                 170                 175

Glu Arg Gln Arg Lys Arg His Lys Ser Asp Ser Ile Ser Leu Ser Phe
            180                 185                 190

Asp Glu Ser Leu Ala Leu Cys Val Ile Arg Glu Ile Cys Cys Glu Arg
        195                 200                 205
```

```
-continued

Ser Ser Ser Ser Glu Ser Thr Gly
    210                 215
```